US011140959B2

(12) United States Patent
Bahrami

(10) Patent No.: US 11,140,959 B2
(45) Date of Patent: Oct. 12, 2021

(54) SYSTEM FOR AND METHOD OF CONTAINING UNPLEASANT ODORS DURING TRAVEL

(71) Applicant: Whoman Bahrami, Washington, DC (US)

(72) Inventor: Whoman Bahrami, Washington, DC (US)

(\*) Notice: Subject to any disclaimer, the term of this patent is extended or adjusted under 35 U.S.C. 154(b) by 184 days.

(21) Appl. No.: 16/395,174

(22) Filed: Apr. 25, 2019

(65) Prior Publication Data
US 2019/0246762 A1 Aug. 15, 2019

Related U.S. Application Data

(63) Continuation-in-part of application No. 15/435,192, filed on Feb. 16, 2017, now abandoned.

(51) Int. Cl.
| | |
|---|---|
| B65D 81/24 | (2006.01) |
| A45C 13/02 | (2006.01) |
| A45C 7/00 | (2006.01) |
| A45C 13/10 | (2006.01) |
| B65D 30/06 | (2006.01) |
| B65D 33/06 | (2006.01) |
| B65D 33/25 | (2006.01) |
| B65D 33/28 | (2006.01) |

(Continued)

(52) U.S. Cl.
CPC .............. *A45C 13/02* (2013.01); *A45C 3/001* (2013.01); *A45C 3/12* (2013.01); *A45C 7/0059* (2013.01); *A45C 7/0063* (2013.01); *A45C 13/103* (2013.01); *A45C 13/1046* (2013.01); *A45F 3/02* (2013.01); *A61L 9/014* (2013.01); *B01D 53/0407* (2013.01); *B65D 29/04* (2013.01); *B65D 33/06* (2013.01); *B65D 33/2508* (2013.01); *B65D 33/28* (2013.01); *A45C 2003/002* (2013.01); *A45C 2003/008* (2013.01); *A45C 2013/026* (2013.01); *A45C 2013/1015* (2013.01); *A61L 2209/14* (2013.01); *B01D 2253/102* (2013.01); *B01D 2253/34* (2013.01); *B01D 2257/80* (2013.01); *B01D 2257/90* (2013.01); *B01D 2258/06* (2013.01); *B01D 2259/4541* (2013.01)

(58) Field of Classification Search
CPC .... B65D 29/04; B65D 33/06; B65D 33/2508; B65D 33/28; B65D 81/22; B65D 81/24; B65D 81/26; B65D 81/267; A45C 3/001; A45C 3/12; A45C 7/0059; A45C 7/0063; A45C 13/02; A45C 13/103; A45C 13/1046; A45C 2003/008; A45C 2013/1015
USPC .............. 206/204, 205, 315.1; 150/106, 107
See application file for complete search history.

(56) References Cited

U.S. PATENT DOCUMENTS

| | | | | |
|---|---|---|---|---|
| 2,537,196 | A | * | 1/1951 | Tanski ................... A24F 23/02 312/31.2 |
| 4,629,064 | A | * | 12/1986 | Barner .................. B65D 31/04 206/204 |

(Continued)

*Primary Examiner* — Luan K Bui
(74) *Attorney, Agent, or Firm* — Steven M. War, Esq.

(57) ABSTRACT

The present invention discloses a sack comprising a second container and a first container, an activated carbon filter that is positioned between said first and second containers and a sealable rubberized zipper and the activated carbon filter is positioned such that it may absorb at least a portion of odor and moisture from items stored inside sack. In addition, an antimicrobial material may be infused into the material of the sack.

7 Claims, 25 Drawing Sheets

(51) Int. Cl.
*A61L 9/014* (2006.01)
*A45C 3/00* (2006.01)
*B01D 53/04* (2006.01)
*A45C 3/12* (2006.01)
*A45F 3/02* (2006.01)

(56) References Cited

U.S. PATENT DOCUMENTS

| | | | | |
|---|---|---|---|---|
| 4,742,908 | A * | 5/1988 | Thomas, Jr. | B65D 81/264 |
| | | | | 206/204 |
| 5,171,523 | A * | 12/1992 | Williams | A61L 2/18 |
| | | | | 206/205 |
| 5,845,769 | A * | 12/1998 | Yeager | B65D 31/12 |
| | | | | 206/204 |
| 6,530,471 | B1 * | 3/2003 | Tsuyuguchi | B65D 81/264 |
| | | | | 206/204 |
| 9,226,557 | B2 * | 1/2016 | Sullivan | A45C 3/06 |
| 2017/0304474 | A1 * | 10/2017 | Drake | A45C 5/03 |

* cited by examiner

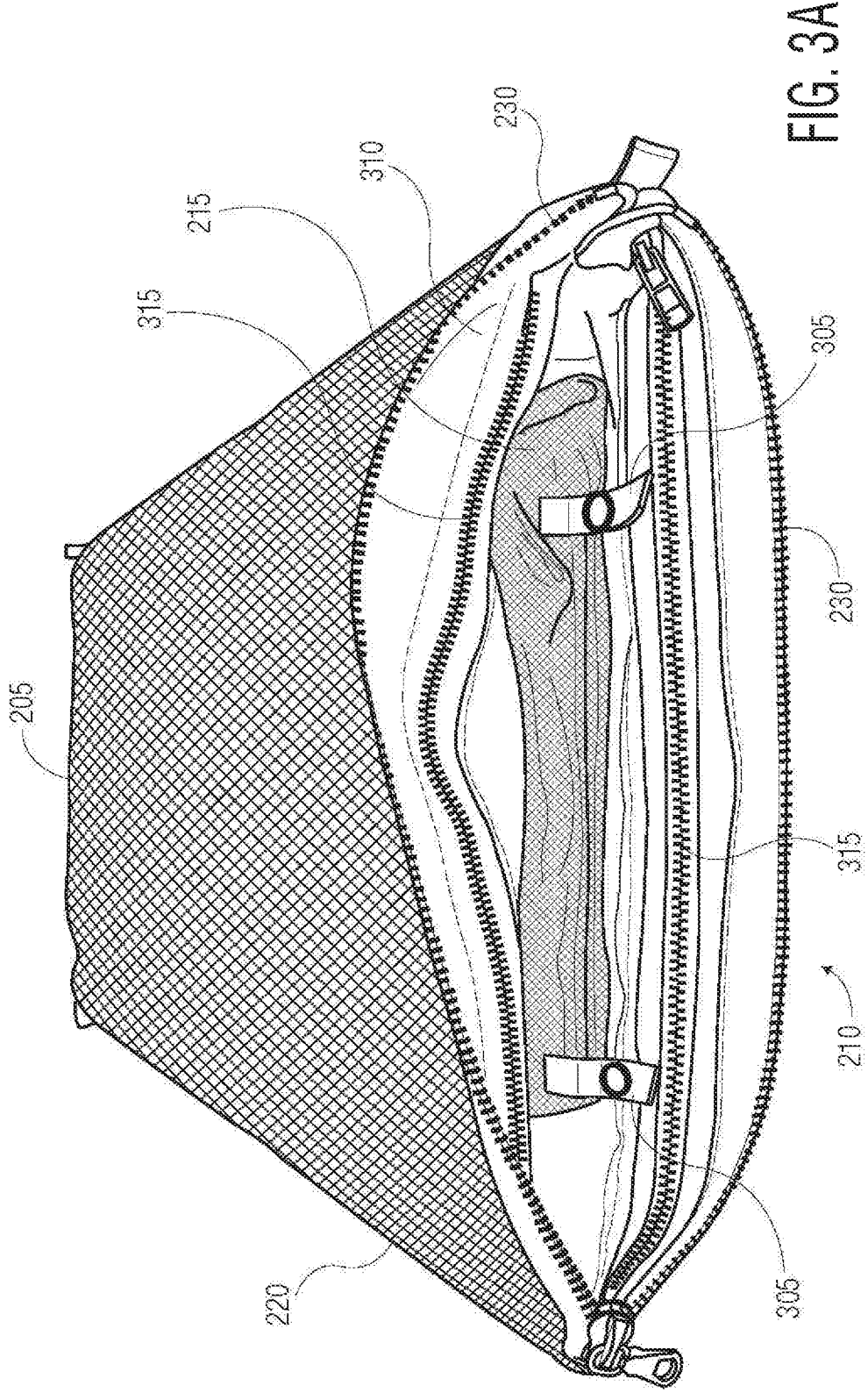

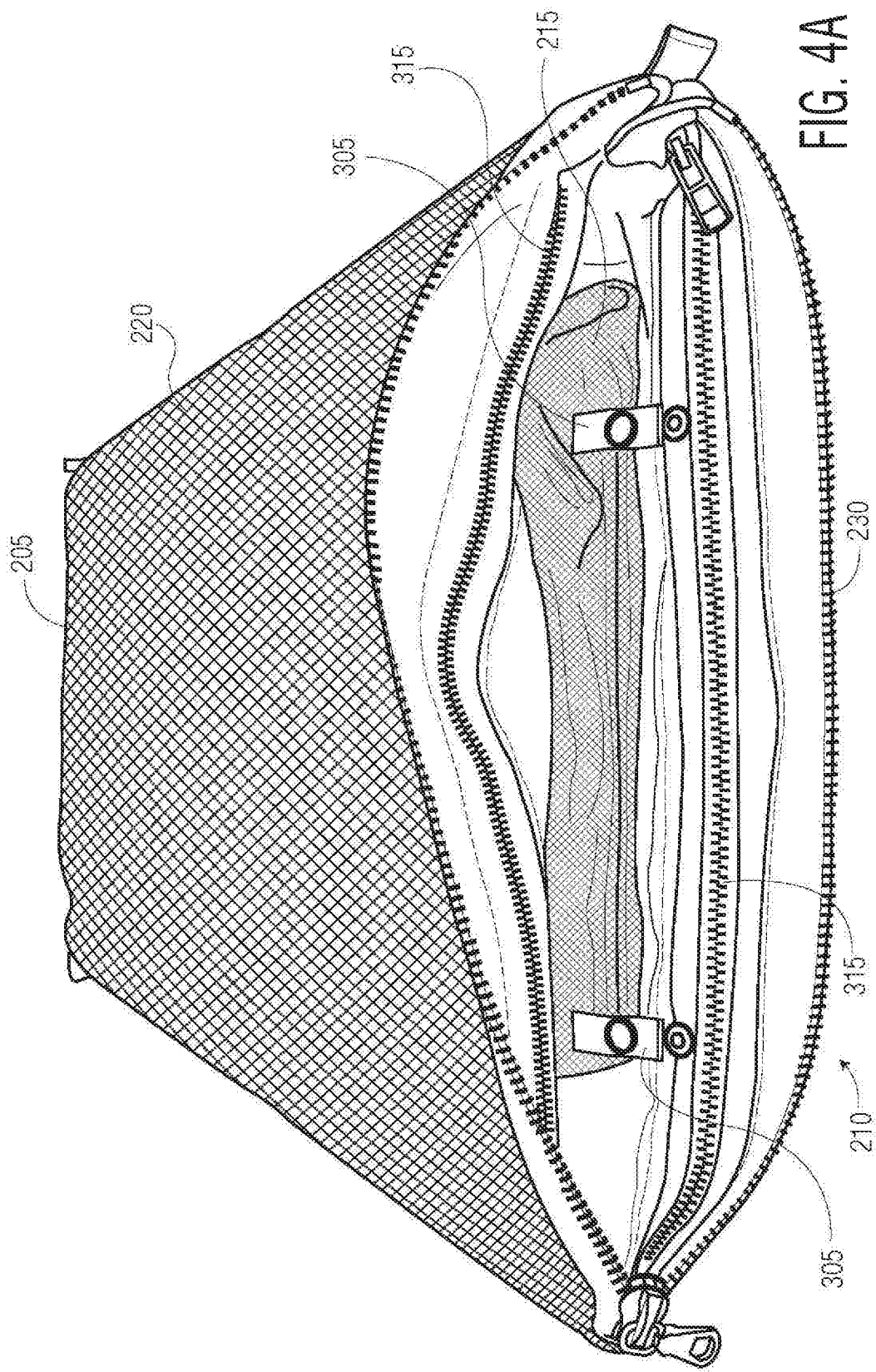

SYSTEM FOR AND METHOD OF CONTAINING UNPLEASANT ODORS DURING TRAVEL

TECHNICAL FIELD

The present disclosure relates to using activated carbon, antimicrobial material or a combination of both in a new type of container to reduce or prevent odors from items stored within the container from permeating to and effecting clothing or possessions outside of the container.

BACKGROUND OF THE INVENTION

One of the most vexing parts of traveling or backpacking is managing what to do with, and how to store, dirty or worn clothing, shoes or anything odorous while we are away from home. Since most of us have clothing which is not disposable and must be kept for future use, many of us come up with inadequate ways of dealing with this problem.

Most of today's travelers favor small easily portable luggage or bags which will fit into the overhead compartments of planes. They also favor this type of luggage to avoid paying baggage check-in fees. However, to have all their necessary belongings fit into such bags, travelers tend to compress all their belongings into small pieces of luggage. Often in the midst of their travel they are forced to compress their dirty worn clothing with clean clothing. As a result, clean clothing will often smell as if it is dirty or it has already been worn.

To prevent smell contamination, travelers use reuse plastic shopping bags to store the dirty or odorous clothing as a way to separate and isolate dirty items from clean items. Although this method does create a separation, it can lead to greater problems. For example, it can cause worn and/or perspired clothing to develop mold because of the damp concealed environment it creates. Touching, wearing or inhaling mold and mildew can cause a wide range of health problems in both allergic and non-allergic people. Concentrating odorous items in one area does not solve the problem and in effect it simply concentrates the odor. Plastic shopping bags are typically closed by tying the handles together. While tying the handles may prevent items inside the bag from falling out, it does not prevent the smell inside the bag from permeating to and effecting clothing or possessions outside of the container.

Hiking backpacks or traveling suitcases often have several different compartments. Travelers often use one or more of these compartments (usually the outside compartments) to store dirty clothing as they travel. Over time, this causes those compartments to smell or become designated dirty compartments. Subsequently, the use of those compartments becomes limited to only being used for dirty clothing or belongings and nothing else. When there are no more compartments or compartment space left to separate clean from dirty clothing, the remaining clean clothing is eventually stored with dirty clothing causing the clean clothing to smell like the dirty clothing.

Because of the size of typical washing machines, it is very difficult to wash luggage or large hiking backpacks after use. Since many of us only own a few pieces of luggage, we typically reused them over and over to pack our clean items regardless if the luggage/backpack is clean, despite their smell or prior use. As a result, in some instances we reach our travel destination wearing fresh clothing that nonetheless smells like the dirty clothes that were stored in the luggage previously.

Triathlons, bicycle races, or group runs are usually located in very rural or remote places and often require hours of travel. The exertion from these events causes participants to sweat extensively. Afterwards, they are left with the dilemma of how to store the clothing which they sweated in for hours until they return home. Packing such clothing in any luggage or backpack is not hygienic and can create mold. In some instances participants will air out their clothing in their cars or even sprawl their dirty clothing through their windows.

This problem of handling dirty or worn clothing does not only affect travelers but also daily commuters. Individuals who commute to work and take with them their gym shoes and clothing, lunch or other items are faced with the dilemma of how to store worn or sweaty gym clothes and shoes with their other possessions. Whether they wear their gym clothes in the morning, during lunch or after work, they are forced with having to return sweaty clothing and shoes home so they can be washed. Often times, these items are brought home in the same bag or backpack used to pack clean gym clothes, books, work material or lunch for the next day.

Shoes are the dirtiest things we own. They touch things we don't want to touch with our hands or clothes. In addition to being dirty, the insides of the shoes are usually odorous from repeated use and perspiration. Because of this, they are often the most inconvenient thing for commuters to pack when needed. Because most people go to the gym before work, during lunch or after work, commuters must often develop ways to separate them by putting them in plastic bags, tying them to the outside of their packs or put them in the outside pockets of their backpacks.

Floor exercises such as yoga have become more popular than ever in recent years. Unfortunately, most gym bags are not designed to accommodate everyday gym clothes, shoes and large floor mats such as yoga mats. This means that in addition to the purses, totes or gym bags already carried, commuters must also carry a separate bag for their floor mats. The existing gym bags or backpacks which can accommodate all these items are too large, cumbersome and they limit mobility. They are also firmly shaped, cannot be collapsed or be packed themselves into anything and remain large even when empty. Commuters who must stand in crowded trains often squeeze these, at times, odorous gym items in their everyday purses or backpacks to avoid hauling around these large gym bags.

The problem with separating odorous items extends beyond commuters but also everyday parents. A lot of new parents who are out in public are forced to change a diaper on the fly and are suddenly faced with the choice of where to dispose of a disposable diaper. In many instances, parents are unable to dispose of dirty diapers in many trash cans because of their lack of degradability. As a result, parents are forced to carry around dirty diapers in their strollers until they can safely dispose of the item at home.

In many of the above instances travelers, backpackers, athletes, and parents are left no alternative, but to bring with them strong chemical filled sprays to mask orders. These items can range from cologne, body sprays, or fabric softeners. Oftentimes these sprays can also stain the clothing.

SUMMARY OF THE INVENTION

The present invention discloses various embodiments of a sack, carrying case, or container (referred to herein as a "sack") which includes a first container and a second container where an activated carbon filter is positioned in the space between the first container and the second container to absorb odors from worn clothing or other items placed inside the first container, or a single container sack with antimicrobial additives infused in the container material and fitted with an activated carbon filtered air release valve. This sack comes in three main embodiments, a non-extendable embodiment, an extendable embodiment and a non-extendable single container embodiment.

In the non-extendable embodiment of the present invention, the first container is always positioned inside the second container and access to both the first and the second container is through a rubberized zipper in the top portion of the sack or carrying case. In this embodiment, the activated carbon filter is inserted through the rubberized zipper and inserted in the space between the first container and the second container so that it is in position to absorb odors from any items placed in the first container. In the non-extendable embodiment, the activated carbon filter may be contained in a separate mesh filter container, or it may be contained in a compartment attached to the outside of the first container or attached to the inside of the second container.

The extendable embodiment of the present invention permits two separate configurations, a non-extended configuration and an extended configuration. In the non-extended configuration, the first container is positioned inside the second container.

However, when the sack is in its extended configuration, the first container is located adjacent to the second container. The extendable embodiment is preferably, a rectangle sack including a first container accessible through a top opening and a second container accessible through a bottom opening. A top portion of the first container is attached to a portion of the rectangular sack. In some embodiments the first container is removably attached to a portion of the rectangular sack. An activated carbon filter is positioned within a mesh filter container which is located in the space between the outside of the first container and the inside of the second container. In the extendable embodiment, the activated carbon filter may be contained in a separate mesh filter container, or it may be contained in a compartment attached to the inside of the second container.

The bottom opening can be opened or closed by use of a bottom sealable rubberized zipper. Similarly, the top opening can be opened or closed by use of a top sealable rubberized zipper. The activated carbon filter is positioned such that it may absorb at least a portion of odor and moisture from items stored inside the first container in the non-extended configuration. The first container can be pushed out (to the extendable configuration) to create a larger sack. In this configuration, the first container becomes an outer portion of the sack doubling the size, and the capacity of the sack, to hold material within it.

In the non-extendable single container embodiment of the present invention, the container is accessible through either a rubberized zipper, a draw string, or a roll-top opening in the top portion of the sack. In this embodiment, the sack material is infused with antimicrobial additives to combat the formation of bacteria and fungi inside the sack. The sack may be made of 1 of 3 fabrics/materials, a fabric, fabric with Thermoplastic Polyurethane (TPU) lining, or of a TPU entirely. In each case, antimicrobial additives may be embedded into the fabric/material during the manufacturing process.

The non-extendable single container embodiment can also be fitted with an air valve to permit the sack to deflate when squeezed into densely packed luggage or backpacks. Allowing the sack to deflate not only creates space but it also deprives mold spores the oxygen needed to grow and promotes greater surface area contact between the bag's antimicrobial material and the contents of the sack. Additionally, the air valve is fitted with a removable odor absorbing activated carbon filter located inside the sack at the air entrance of the valve. The activated carbon filter removes odor and moisture from the exiting air and from permeating to and effecting clothing or possessions outside of the sack, allowing the traveler to pack dirty and clean items as closely as they desire. The filter can be removed for replacement or to wash the sack and the valve maybe be sealed by twisting the cap of the valve if the user wished to deflate the sack itself or desires to keep the bag inflated.

BRIEF DESCRIPTION OF THE DRAWINGS

The drawings are meant to illustrate the principles of the invention and do not limit the scope of the invention. The above-mentioned features and objects of the present disclosure will become more apparent with reference to the following description taken in conjunction with the accompanying drawings wherein like reference numerals denote like elements in which:

FIGS. 3A, 3B, 3C, 3D, and 3E are drawings illustrating the steps in inserting the activated carbon filter in the mesh filter container of the extendable embodiment of the sack while the sack or container is in its non-extended configuration;

FIGS. 4A, 4B, 4C, 4D, and 4E are drawings illustrating the extendable embodiment of the sack in various embodiments of an extended configuration;

DETAILED DESCRIPTION OF THE INVENTION

The present invention relates to a sack or similar container which can be used to store and reduce, or absorb, the odor of anything placed inside it.

Non-Extendable Embodiment

Figure 1:
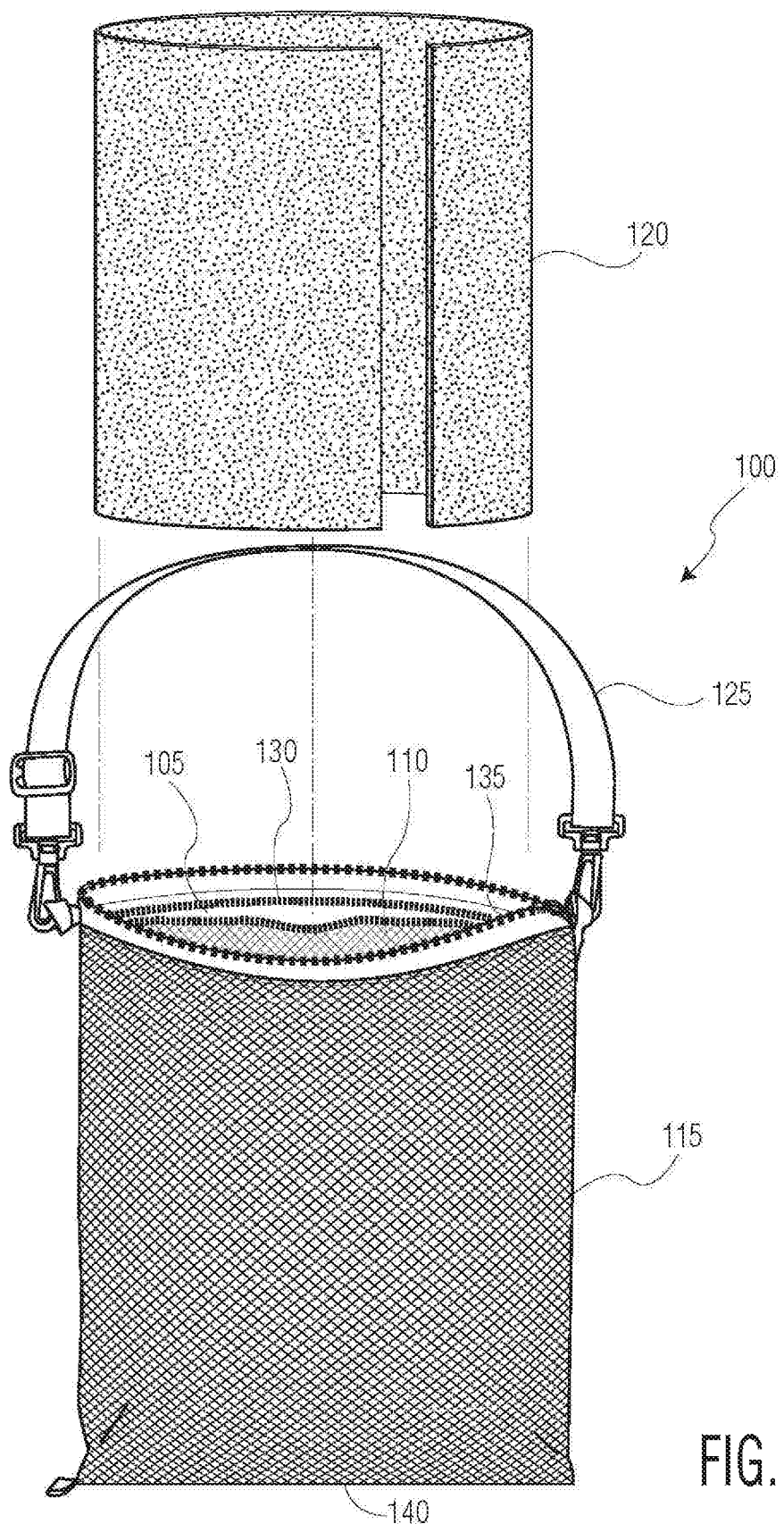
FIG. 1 is an illustration of a non-extendable embodiment of the present invention wherein access to both the first and second container are through the top sealable rubberized zipper.

Referring now to FIG. 1, a non-extendable embodiment of the sack 100 of the present invention includes a top opening 105, a first container 110, a second container 115, an activated carbon filter 120, and a strap 125. The first container 110 includes a first sealable rubberized zipper 135. The second container 115 includes a zipper 130. Preferably, the zipper 130 that holds the activated carbon filter in place would be a circumferential zipper—meaning it goes around the inside of the sack 100. In this non-extendable embodiment, the activated carbon filter 120 is inserted into the top opening 105 and positioned between the outside wall of the first container 110 and the inside wall of the second container 115 in a mesh filter container which is built into the outside portion of the first container 110 or the mesh filter container is built into the inside portion of the second container 115. Alternatively, a separate mesh filter container (not shown) could be included. In this embodiment, the bottom 140 of the sack 100 is closed. One of ordinary skill in the art would appreciate that the sealable rubberized zipper 130 may be replaced with other methods for closing the first container such as rolling closure with locking buckle, or similar methods.

Extendable Embodiment

Figure 2:
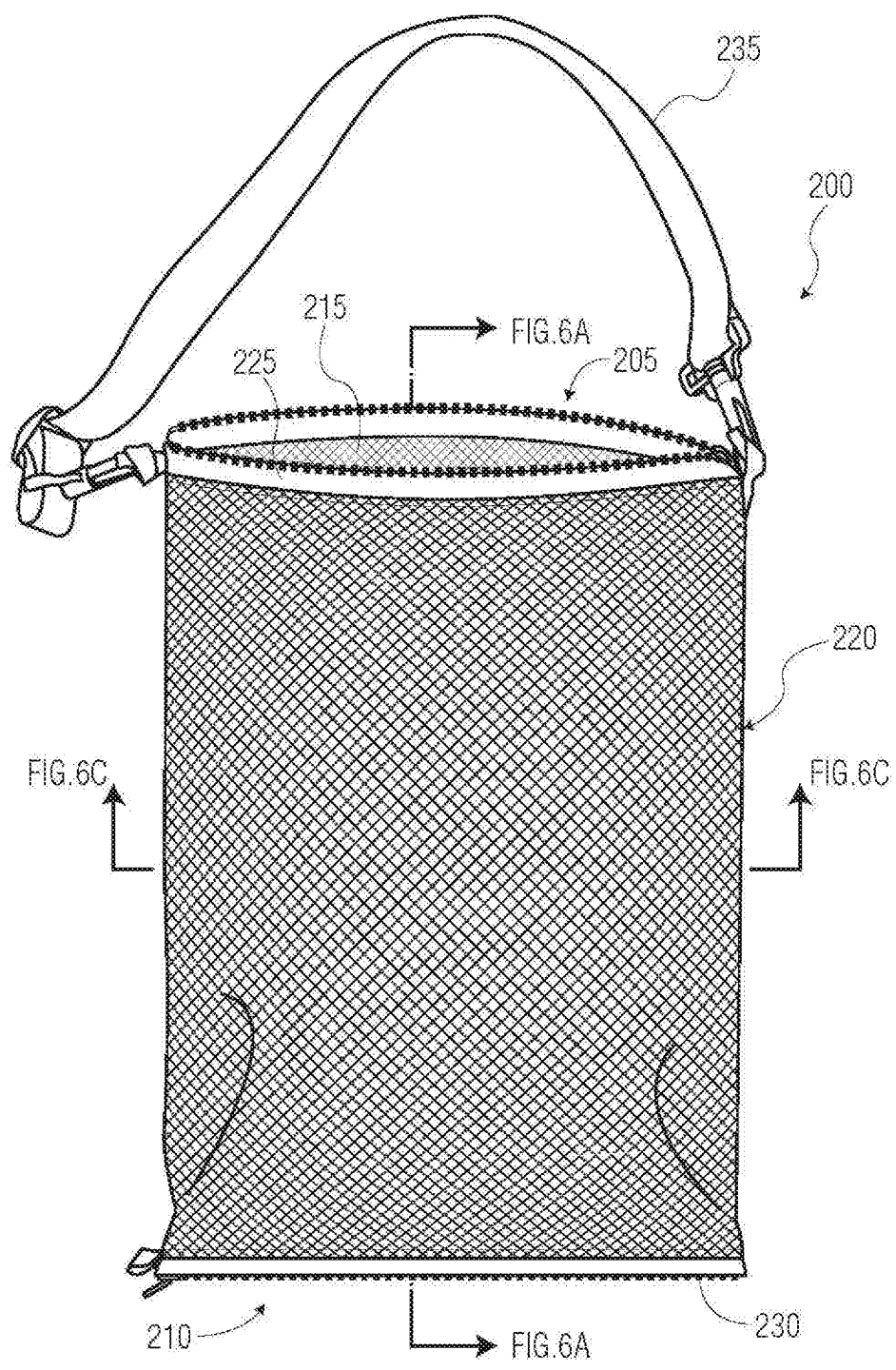
FIG. 2 is an illustration of an extendable embodiment of a sack or container of the present invention in its non-extended configuration.

Referring now to FIG. 2, in another embodiment, the invention is preferably a rectangular sack 200 with two sealable openings, a top opening 205 and a bottom opening 210. The size of the sack was selected to easily accommodate up to men's size 12 sneakers. The shape of the rectangular sack 200 is preferable because the vast majority of travel packs are rectangular in shape (suit cases, duffle bags, luggage, carryon luggage, backpacks etc.) and configuring the current invention in the shape of a rectangle allows the sack to be easily packable within other luggage. Most major airlines require the sizing limits of carry-on bags and personal items to rectangular shaped luggage. The sack is designed to fit conveniently into the luggage limits (carry on and personal item) of all major airlines.

The design of the sack 200 includes a first container 215 and a second container 220. Both containers. i.e., the first container 215 and the second container 220, serve different purposes. In this extendable embodiment, the first container 215 of the sack 200 is used to store or house smaller odorous items in its non-extended configuration which are inserted through a top sealable rubberized zipper 225 located at the top of the sack 200.

In this extendable embodiment, there are two access points to the first container 215. The first access point is from the top opening 205 through the top sealable rubberized zipper 225. This access point permits the user to insert items, such as shoes, work out clothing, etc. into the interior of the first container 215 when it is in its non-extended configuration. Access through the top opening 205 (when it is in its non-extended configuration) provides space for objects the size of the sack (in its non-extended configuration) itself or smaller.

Figure 4B:
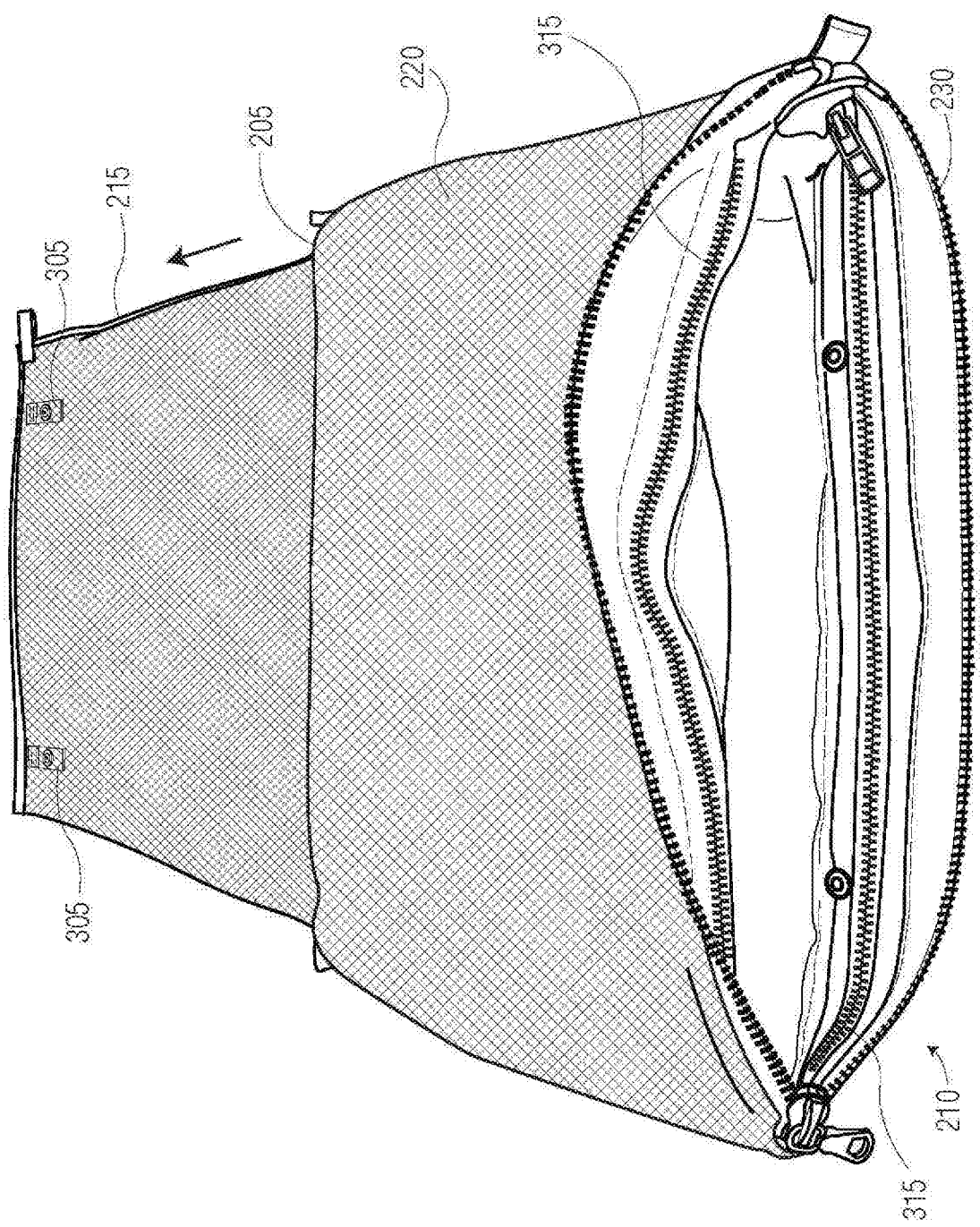

The second access point to the first container 215 is through the bottom opening 210. While access through the bottom opening 210 permits access to the first container 215 itself, it does not permit access to the inside of the first container 215 when the sack is in its non-extended configuration. However, as one of ordinary skill in the art would appreciate, the bottom opening 210 does permit access to the inside of the first container when the sack is in its extended configuration (FIG. 4B).

In the extendable embodiment of the present invention, the bottom opening 210 also provides access to the space between the outside of the first container 215 and the inside of the second container 220 through the bottom sealable rubberized zipper 230 when the sack is in its non-extended configuration. The bottom opening 210, again through the bottom sealable rubberized zipper 230, also provides access to the mesh filter container 310 (FIG. 3B) which includes its own filter container zipper 315 which houses the activated carbon filter 300 in the extendable embodiment. Preferably, filter container zipper would be a circumferential zipper—meaning it goes around the inside of the sack 100. Filter container zipper 315 goes around the entire inside of the second container 220. When filter container zipper 315 is unzipped, the mesh filter container is accessible. When filter container zipper 315 is zipped, the user has access to the inside outside of the first container 215 through the bottom sealable rubberized zipper 230. Additionally, filter container zipper 315 must be opened to insert the activated carbon filter 300 and when the filter container zipper 315 is closed it holds the activated carbon filter 300 in place.

Figure 3B:
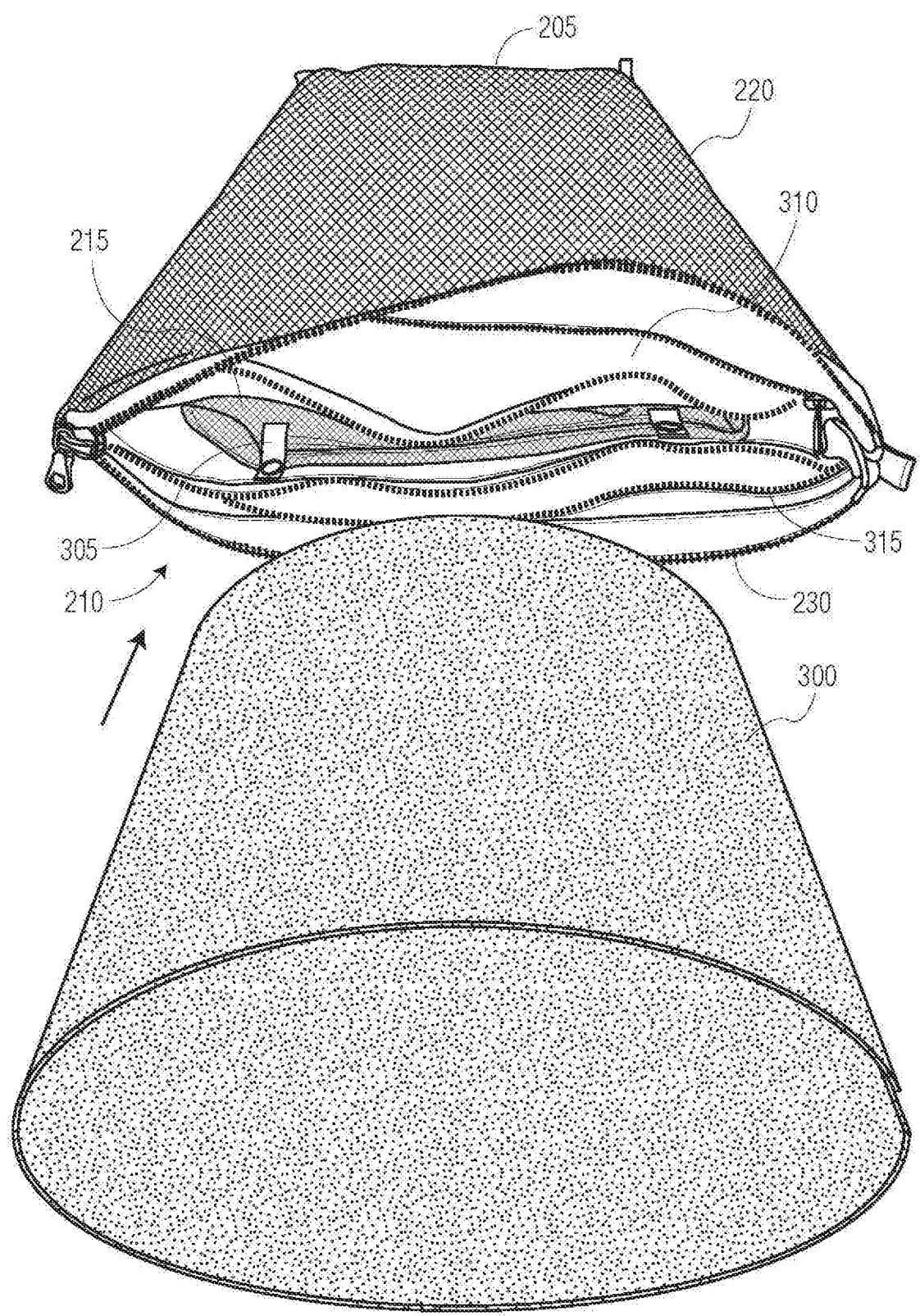
Figure 3C:
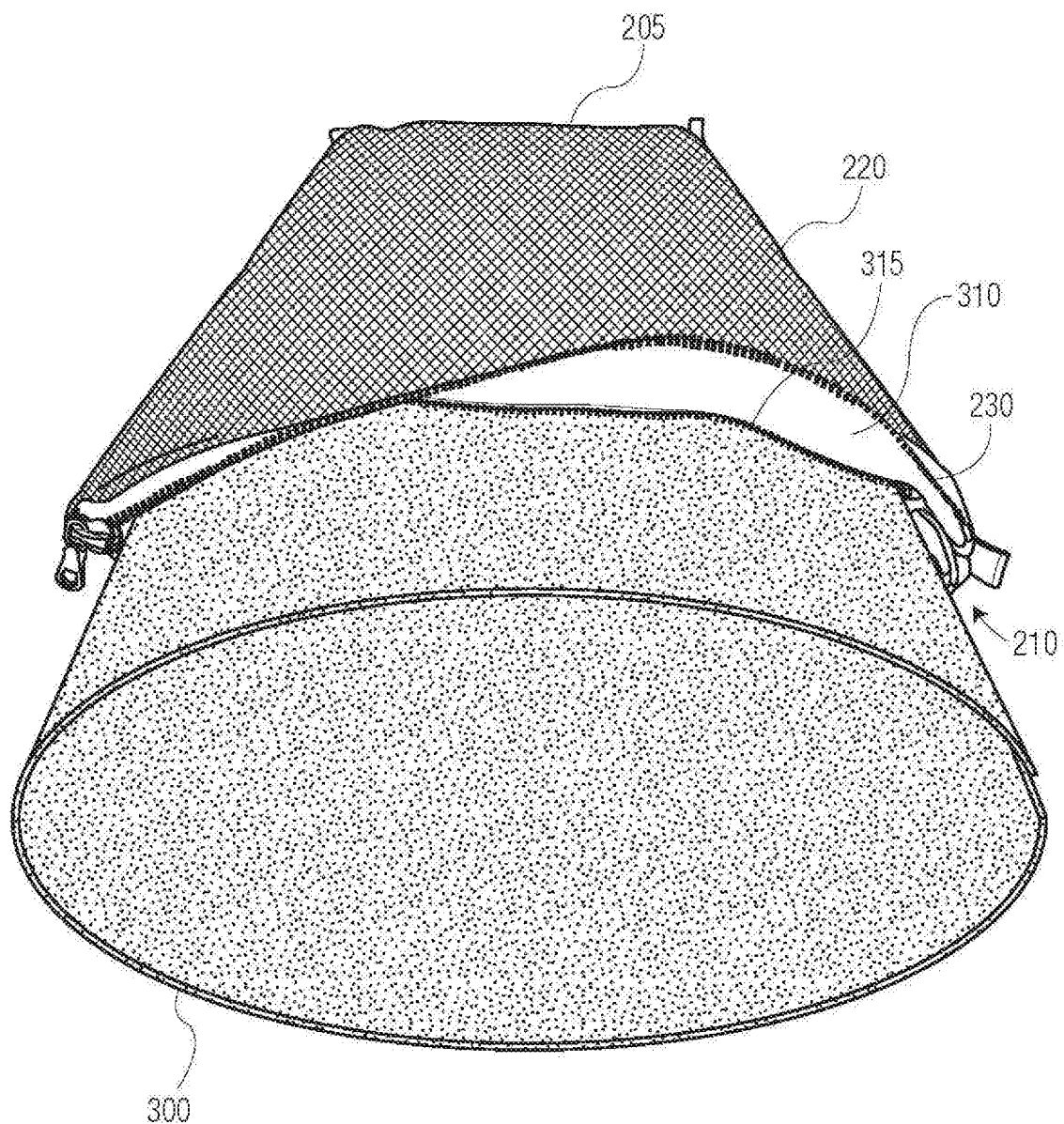
Figure 3D:
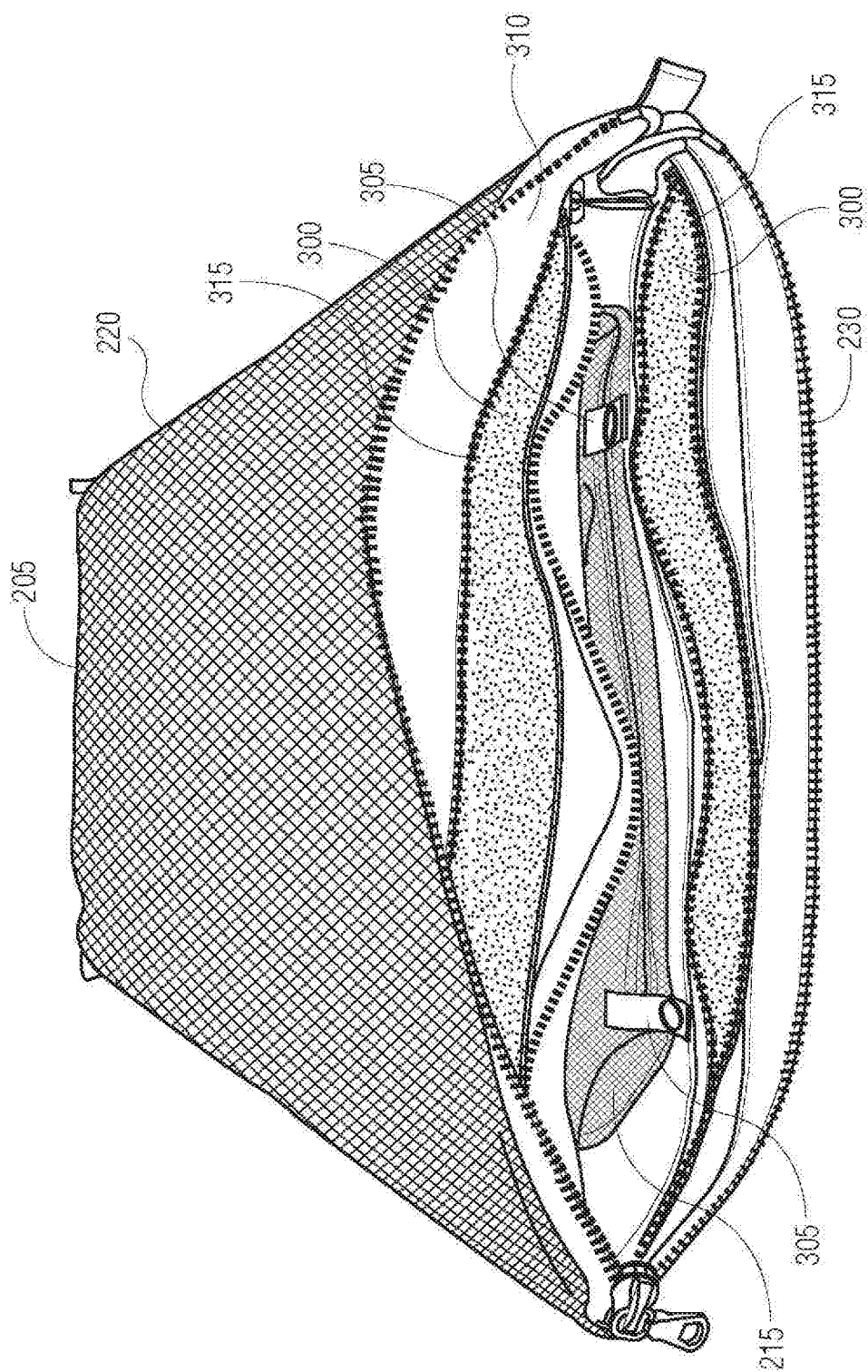
Figure 3E:
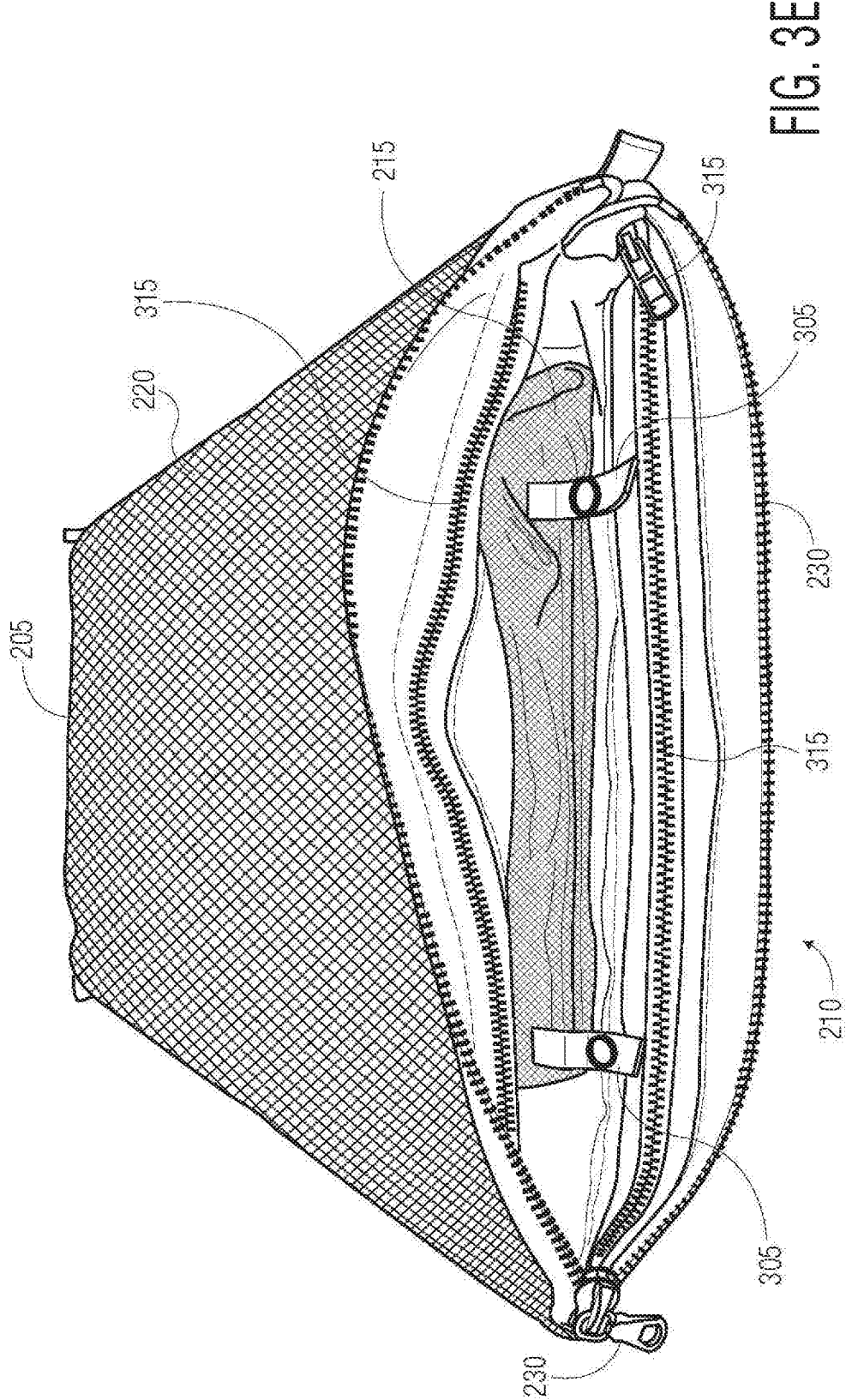

Referring now to FIGS. 3A-3E, to insert the activated carbon filter 300, the bottom sealable rubberized zipper 230 is unzipped (FIG. 3A) giving the user access to the filter container zipper 315 and the outside of the first container 215 which is attached to the mesh filter container 310 by two fastening snaps 305 (in the non-extended configuration). The mesh filter container 310 can be opened by unzipping the filter container zipper 315 (FIG. 3B) thereby permitting the user access into inside of the mesh filter container 310. The activated carbon filter 300 is then inserted into the mesh filter container 310 (FIG. 3C). The activated carbon filter 300 is inserted preferably by folding it in half. The activated carbon filter 300 should be inserted through the opening of the filter container zipper 315 and completely lines the inside of the second container 220. Once it has been determined that the activated carbon filter 300 completely lines the inside of the second container 220 and is positioned within the mesh filter container 310, the filter container zipper 315 may be closed to conceal the activated carbon filter 300. Once the activated carbon filter 300 is inserted into the mesh filter container 310 (FIG. 3D) the filter container zipper 315 is closed thereby enclosing the activated carbon filter 300 inside the mesh filter container 310 which as indicated previously, is located in the space on the inside of second container 220 and the outside of the first container 215 (FIG. 3E).

Odorous items may now be placed into the first container 215 of the sack 200 through the top opening 205 (in the non-extended configuration) or through the bottom opening 210 (in the extended configuration), depending on the volume of storage needed. Once odorous items are inserted into the first container 215, the top sealable rubberized zipper 225 (in the non-extended configuration) or the bottom sealable rubberized zipper 230 (in the extended configuration) may now be closed to conceal the items placed inside the first container 215.

Odors from the items stored within the first container 215 pass through the breathable mesh material of the first container 215 and the breathable mesh material of the mesh filter container 310 where it then interacts with and is absorbed by the activated carbon filter 300. The highly permeable activated carbon filter 300 will also absorb odors of anything placed outside the sack 200 because of the breathable mesh materials used in the second container 220 permit the activated carbon filter 300 to absorb odors which are outside, but close to, sack 200. This also provides breathability for the odorous contents inside the first container 215 and reduces (or eliminates) the formation of mold.

Because items are pushed in and pulled out of the first container 215 (in non-extended state) the first container 215 is secured from moving or being pull out of the sack by two fastening snaps 305 which are located at the bottom of the first container (in non-extended state) and mesh filter container 310. The top of the first container 215 is sewn, or otherwise connected, to the second container 220. The two fastening snaps 305 are connected to hold the first container 215 in place and can be easily disconnected from each other to allow the first container 215 to be pulled out from inside of the sack.

In its non-extended configuration, the activated carbon filter 300 is used to absorb or reduce the smell or odor of items stored within the first container 215. The first container 215 is preferably attached to the sack 200 inside the top opening 205 of the sack 200. This type of attachment permits the first container 215 to be pulled out from inside of the sack 200 (after undoing the fastening snaps 305) while the first container 215 remains attached to the sack 200. When the first container 215 is pulled out from inside the sack 200 the containable size of the sack 200 is effectively doubled.

Because the first container 215 is used to store dirty and odorous items, the sack 200 must be periodically washed. Also, the activated carbon filter 300 must be recharged (in sunlight) or replaced over time as its absorbability diminishes. For this reason, the activated carbon filter 300 can be easily removed from the sack 200 by unzipping the bottom sealable rubberized zipper 230, then unzipping the filter container zipper 315 and pulling the activated carbon filter 300 out.

The activated carbon filter 300 is easily removed through the bottom sealable rubberized zipper 230 and the filter container zipper 315. Easy removal of the activated carbon filter 300 is desirable for at least three reasons. First, periodic removal of the activated carbon filter 300 is necessary to recharge the activated carbon filter 300. Recharging of the activated carbon filter 300 is performed preferably in direct sunlight, thereby extending the useful life of the activated carbon filter 300. Second, removal of the activated carbon filter 300 is desirable so that the sack 200 (without the activated carbon filter 300 inserted) can be washed. Third, removal of the activated carbon filter 300 is necessary so that the activated carbon filter 300 can be replaced at the end of its useful life.

As discussed above, in the non-extended configuration, the top opening 205 permits the insertion of smaller odorous items (such as used exercise clothing). Inserting and removing odorous items into and from the first container 215 in the non-extended configuration does not damage, move, or shift the activated carbon filter 300 when the activated carbon filter 300 is positioned in the mesh filter container 310 located between the inside of the second container 220 and the outside of the first container 215 because the activated carbon filter 300 is constantly secured inside the mesh filter container 310 and the filter container zipper 315.

However, sometimes it is desirable to have a larger sack or container. Opening both the top opening 205, then bottom opening 210 and disconnecting the fastening snaps 305 from the mesh filter container 310, permits reconfiguring the sack 200 to be in its extendable configuration. In the extended configuration, opening the bottom opening 210 permits the insertion of more or larger odorous items (such as athletic equipment).

Ideally, the outside walls of the activated carbon filter 300 may be composed of two types of mesh material. The mesh material on the inner side of the activated carbon filter 300 is the mesh filter container 310 and is made of strong polyester breathable mesh. Conversely, the mesh material on the outside of the activated carbon filter 300 only comes in contact with the inside wall of the mesh filter container 310 and is made of a thick polyester mesh. Both of these types of mesh material (strong polyester mesh and thick polyester mesh) provide the activated carbon filter 300 optimal exposure to odors within the activated carbon filter while preventing odors from escaping from the sack 200 and to the environment. The mesh used also provides breathability so that excess moisture can easily evaporate from the sack 200. As an extra precaution to keep the sack odor free, both the strong polyester mesh and the thick polyester mesh are infused with antimicrobial agents to prevent the growth of odor causing bacterial, mold and mildew. Lastly, the mesh is chosen to protect the items inside and outside the sack 200 from puncturing the activated carbon filter 300 and to protect the activated carbon filter 300 from damage.

Using a top sealable rubberized zipper 225 to close the first container 215 provides several benefits. First, the top sealable rubberized zipper 225 prevents the items stored inside the sack 200 from coming loose or escaping during travel or other handling. Second, the top sealable rubberized zipper 225 provides a method to quickly open or close the first container 215 to add or remove odorous items from first container 215 while hung on the user from the carrying straps 235. Third, the top sealable rubberized zipper 225 prevents unfiltered odors from escaping the first container 215 of the sack 200. Additionally, the top sealable rubberized zipper 225 permits quick and easy opening and closing of sack 200.

This first container 215 is preferably made of highly breathable polyester mesh (FIG. 3B). The breathable polyester mesh material provides very high breathability and provides air to reach the activated carbon filter 300. The activated carbon filter 300 must have access to odorous and moist air in order to absorb either.

The outside layer of the activated carbon filter 300 is made of a breathable polyester mesh material which provides a thick protective barrier between the activated carbon filter and any sharp items which may be located outside the sack 200. The breathable polyester mesh material is the only material that provides such a level of both protective separation and breathability.

The breathable polyester mesh material includes many small holes for added breathability. These holes allow excess moisture to evaporate from the first container 215. As an extra precaution to keep the sack odor free, the polyester mesh is infused with antimicrobial agents to prevent the growth of odor causing bacterial, mold and mildew. The breathable spacer mesh material is also very light while being both durable and flexible so items of various shapes (for example, shoes) can easily fit into the first container 215 or so that the sack 200 can fit inside various baggage environments without tearing. Additionally, the breathable spacer mesh material is washable, which is a requirement since the breathable spacer mesh material frequently comes into direct contact with dirty items stored within the first container 215. The breathable polyester mesh material is also composed of a material which dries very quickly after being washed because the sack 100 preferable cannot be added to dryer machine. Finally, the breathable polyester mesh material includes a smooth texture to prevent or reduce any rubbing which would wear or break down activated carbon filter 300 during movement of sack 200.

The mesh used to construct the mesh filter container 310 also has a smooth texture such that they will not wear or break down the activated carbon filter 300 during movement of the sack 200. In addition, the mesh used to construct the mesh filter container 310 provides very high breathability because the activated carbon filter 300 must be exposed to air to work as an odor and moisture absorber to contents of first container 215 of sack 200. The top sealable rubberized zipper 225 is used so that odor does not escape the sack 200. The highly breathable mesh material is used to allow the odor and moisture from the odorous items stored within the first container 215 to be released freely to the second container 220, and lastly the mesh filter container 310 of the sack 200, both of which are made of highly breathable mesh material. Preferably, polyester is used for the breathable mesh material because it is strong enough to protect the activated carbon filter 300 from excessive loads in the first container 220 and breathable spacer mesh material is used for the second container 235 to provide a thick yet breathable protective barrier from things outside the sack 200.

Preferably, the activated carbon filter 300 is either netted or woven activated carbon material with viscose material applied to both sides to provide strength. The activated carbon filter 300 also provides excellent breathability which permits odorless air to pass between the first container 215 and the second container 220 and the outside of the sack 200. The activated carbon filter 300 is also firm enough from the viscose material so that it does not shift while the sack 200 is handled and items are being placed into it. The viscose backing (both sides) of the activated carbon filter 300 also helps prevent holes from forming in the surface of the activated carbon filter 300 due to friction between the activated carbon filter 300 and the protective mesh lining. Furthermore, the activated carbon filter 300 provides the correct firmness due to its viscose backing so that it can be easily installed through the bottom opening 210 of the sack 200 and in a manner that it completely lines the inside of the breathable spacer mesh material. The use of an activated carbon filter 300 permits these goals to be accomplished.

When configured for use in either the extended or the non-extended configuration, the mesh filter container 310 of the sack 200 contains within it, the activated carbon filter 300. The second container 220 can be opened by the bottom sealable rubberized zipper 230, which, preferably, runs alongside the bottom opening 210 of the sack 200. This second container 220 is made of highly breathable polyester mesh. The bottom sealable rubberized zipper 230 is used so that the unfiltered odor stored in the second container 220 does not escape. The activated carbon filter 300 is inserted by opening the bottom sealable rubberized zipper 230, then opening the filter container zipper 315. The outside layer of the sack 200 is the second container 220 and is made of thick yet breathable mesh material which provides a buffer to protect the delicate activated carbon filter 300 from friction and other items sorted with and around sack 200.

In the nonextended configuration, odorous and damp items are placed in the first container 215. Odor and moisture then pass through the breathable mesh materials of the first container 215 and the mesh filter container 310 and into the activated carbon filter 300 which is located inside the mesh filter container. The activated carbon filter 300 then absorbs the order and moisture of nearly anything located in the first container 215. The highly permeable spacer mesh of the second container 220 also permits the activated carbon filter 300 to absorb odor of anything placed outside in close proximity with the sack.

Because the first container 215 is used to store dirty and odorous items, the sack 200 must be periodically washed. Also, the activated carbon filter 300 must be recharged (in sunlight) or replaced over time as its absorbability diminishes. For this reason, the activated carbon filter 300 can be easily removed from the sack 200 by unzipping the bottom sealable rubberized zipper 230, unzipping the filter container zipper 315 and removing the activated carbon filter 300 from the mesh filter container 310 where it is normally housed.

This sack (or container) 200 is designed this way so that odorous items can be placed through the top sealable rubberized zipper 225 of the sack 200 (in its non-extended configuration) or through the bottom sealable rubberized zipper 230 of the sack 200 (when in its extended configuration) and not directly come into contact with the activated carbon filter 300. In this embodiment, the sack 200 is designed this way to protect the delicate activated carbon filter 300 from the objects placed in the first container 215 while permitting nearly effortless changing of the activated carbon filter 300 within the second container 220.

Figure 4C:
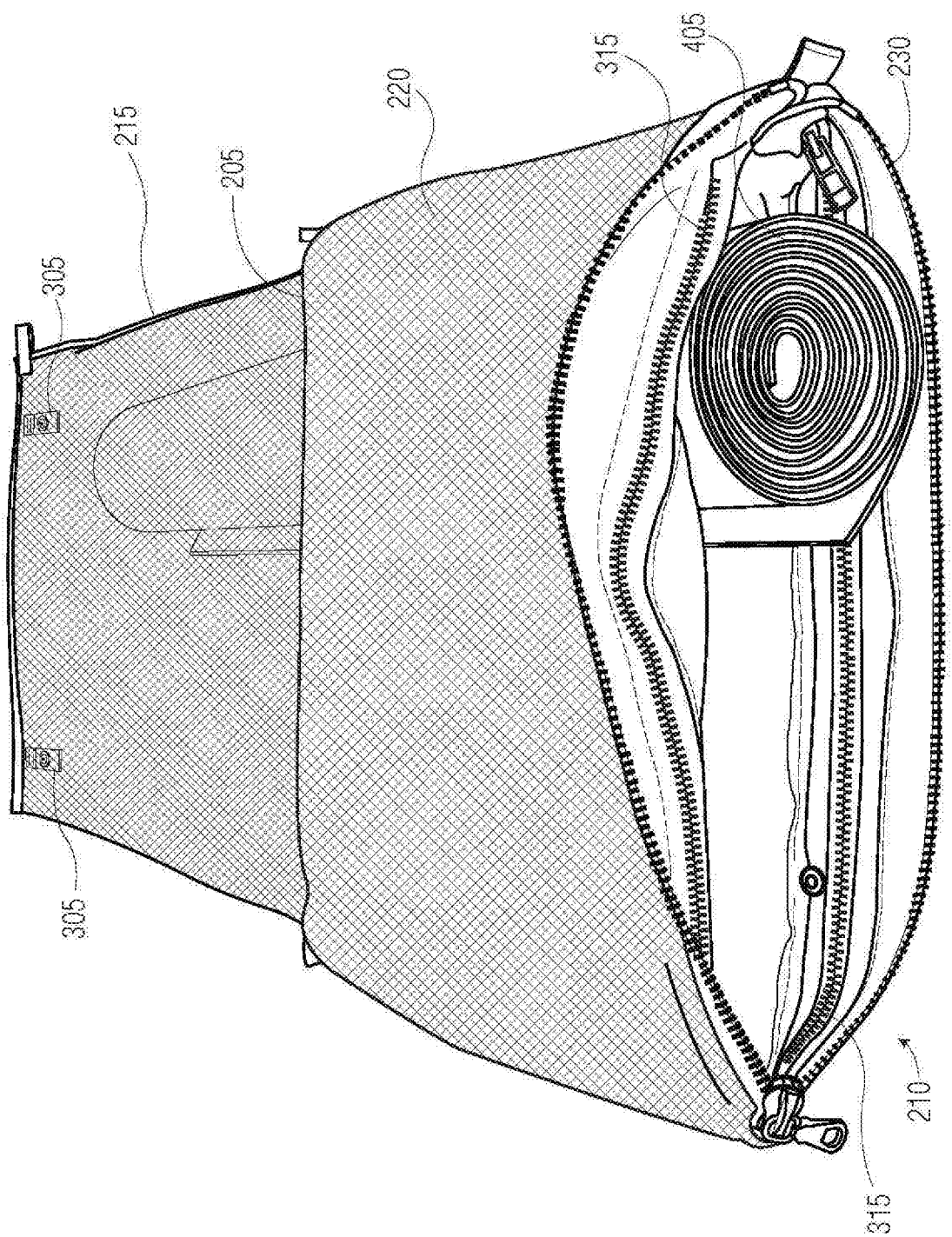
Figure 4D:
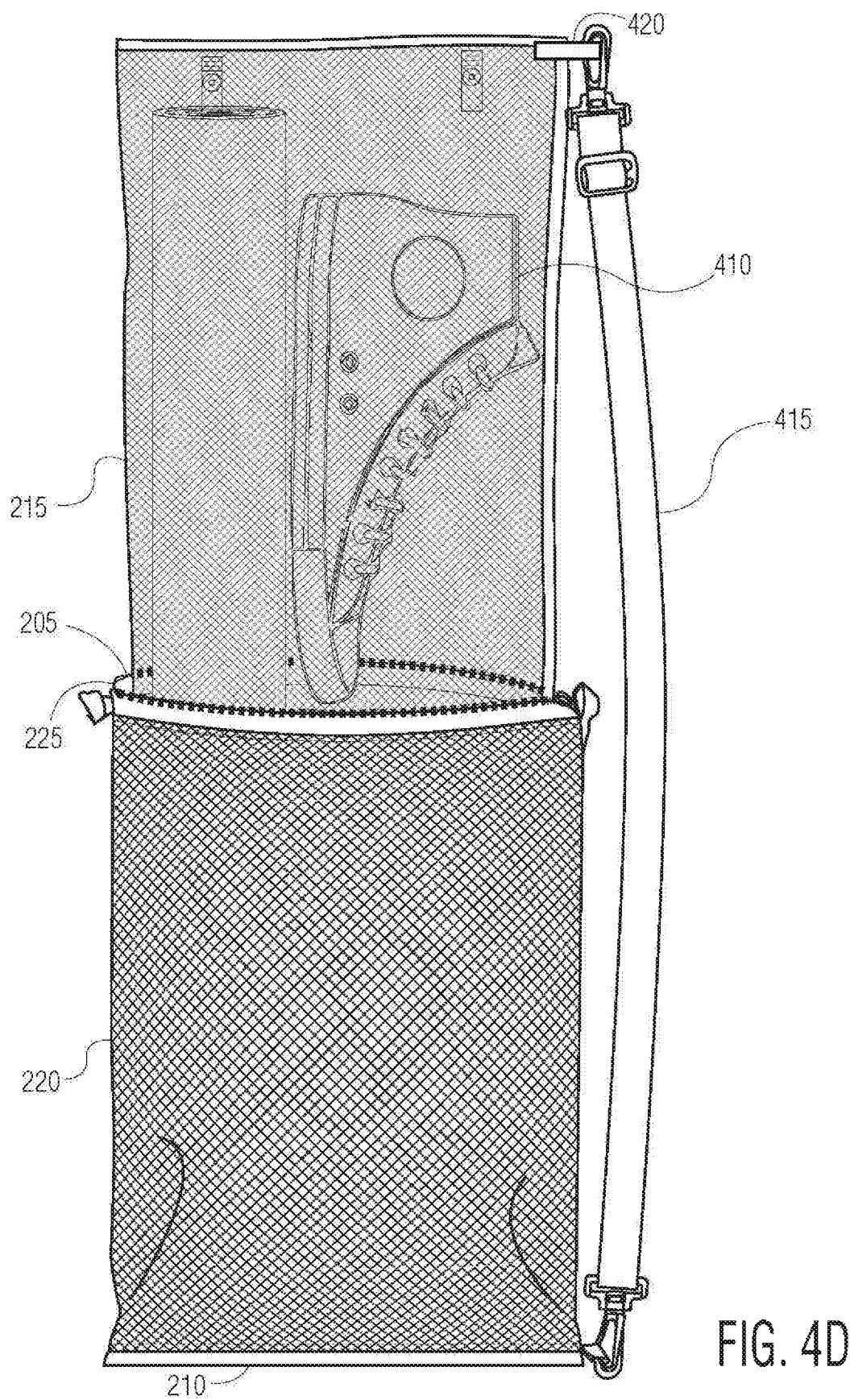
Figure 4E:
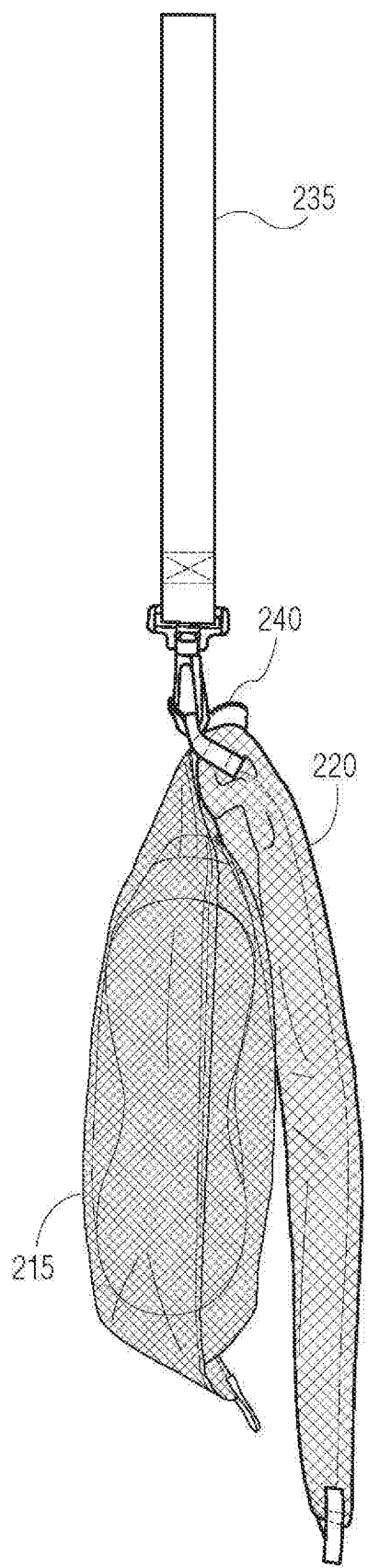

Referring now to FIGS. 4A-4E, the carrying mode and volume sizing of the sack can also be changed. By unzipping the top sealable rubberized zipper 225 and the bottom sealable rubberized zipper 230, detaching the fastening snaps 305, and pulling the portion of the first container 215 that attaches to the fastening snaps 305 from the top opening 205, the user can utilize the first container 215 in an extended state by filling it from the bottom opening 210. In the extended configuration items may also be separated by inserting the items desired to be separate first, folding the second container at the top opening 205, then adding the second group of items to the bottom opening 210 (FIG. 4E).

FIGS. 4B-4E illustrate the sack 200 of the current invention in its extended configuration. FIG. 4B illustrates that the first container 215 can be extended mostly outside the second container 220. In this configuration, the portion of the first container 215 that is normally in the interior of the sack 200 is now mostly outside the second container 220 and clearly visible when the sack 200 is being carried. FIG. 4C shows that, in its extended configuration, the sack 200 can contain larger items which would normally not fit within the sack 200 when it is in its non-extended configuration. For example, FIG. 4C illustrates that the sack 200 in its extended configuration can hold within it, a yoga mat 405 or larger shoes (410 as shown in FIG. 4D). FIG. 4D illustrates an embodiment of the present invention which includes a side strap 415. FIG. 4E illustrates an embodiment of the present invention in its extended configuration (but folded over) which includes a top strap 235.

When a top strap 235 is attached to the top carrying loops 240, the first container 215 (now used as part of the exterior container) can remain folded and lay directly against the outside of the sack 200, creating two separate compartments. This allows the sack 200 to be carried by itself in a compact configuration.

The sack 200 can also carry larger fixed items such as yoga mats in the same extended state but unfolded. In its extended configuration and as shown in FIGS. 4B-4D, the sack 200 contains a carrying loop on the first container. Once extended, carrying straps can be attached to the carrying loop 420 on the first container 215 and at the bottom of the sack or any combination thereof to carry the sack comfortably.

Additionally, one or more snaps (not shown) may be attached to the first container 215 in a manner that would permit "snapping" a portion of the first container 215 to the bottom portion 210 of the sack 200. Snapping a portion of the first container 215 when it is in its extended configuration would be useful to prevent that first portion from moving around when the sack 200 is carried in its extended configuration.

In other embodiments of the present invention, the first container may be removable to permit the replacement of the standard first container with specialized first containers. In these embodiments, the portion of first container 215 that was sewn (or otherwise attached) to the sack would need to be a removable attachment. In other words, a first container made of a first material may be removed and replaced with another container made of a second material. Specialized first containers can be envisioned for specific needs such as preventing wet bathing suits from soaking through to items in the second bag, the use of heavier materials to prevent shoes with metal cleats from puncturing or damaging the first container, and similar specialized applications.

Figure 5A:
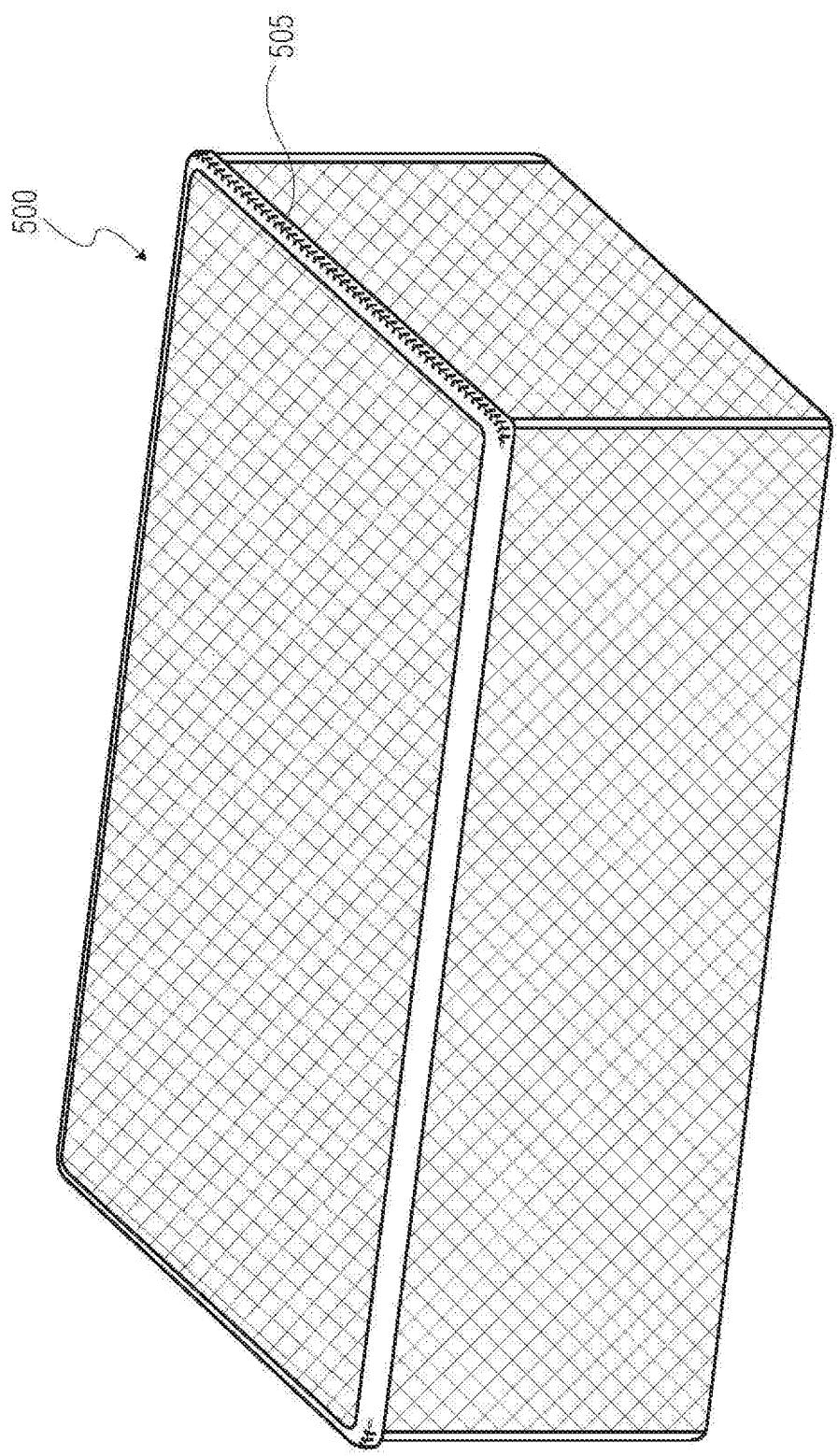
FIGS. 5A, 5B and 5C illustrate another embodiment of the invention in a cubed shaped container.
Figure 5B:
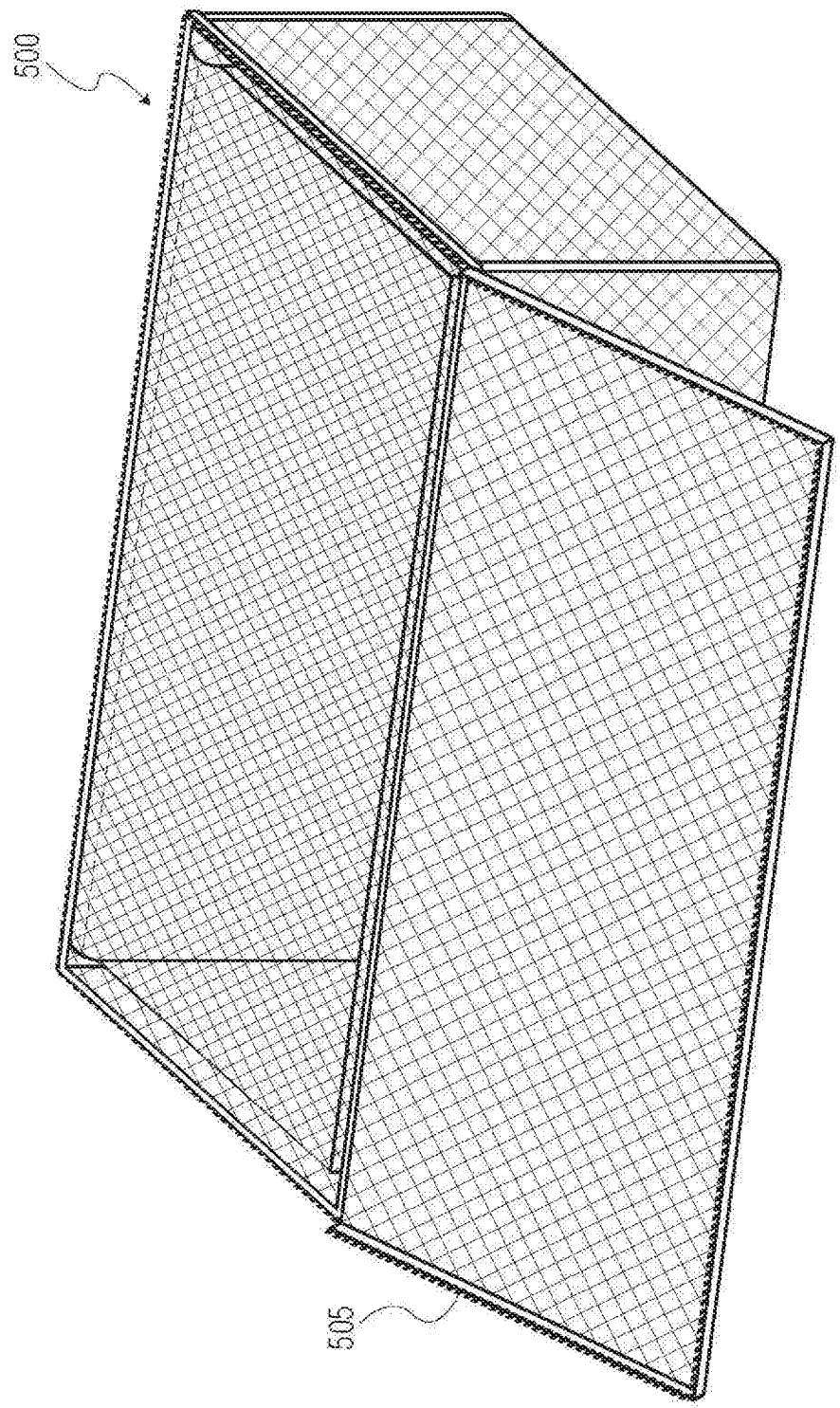
Figure 5C:
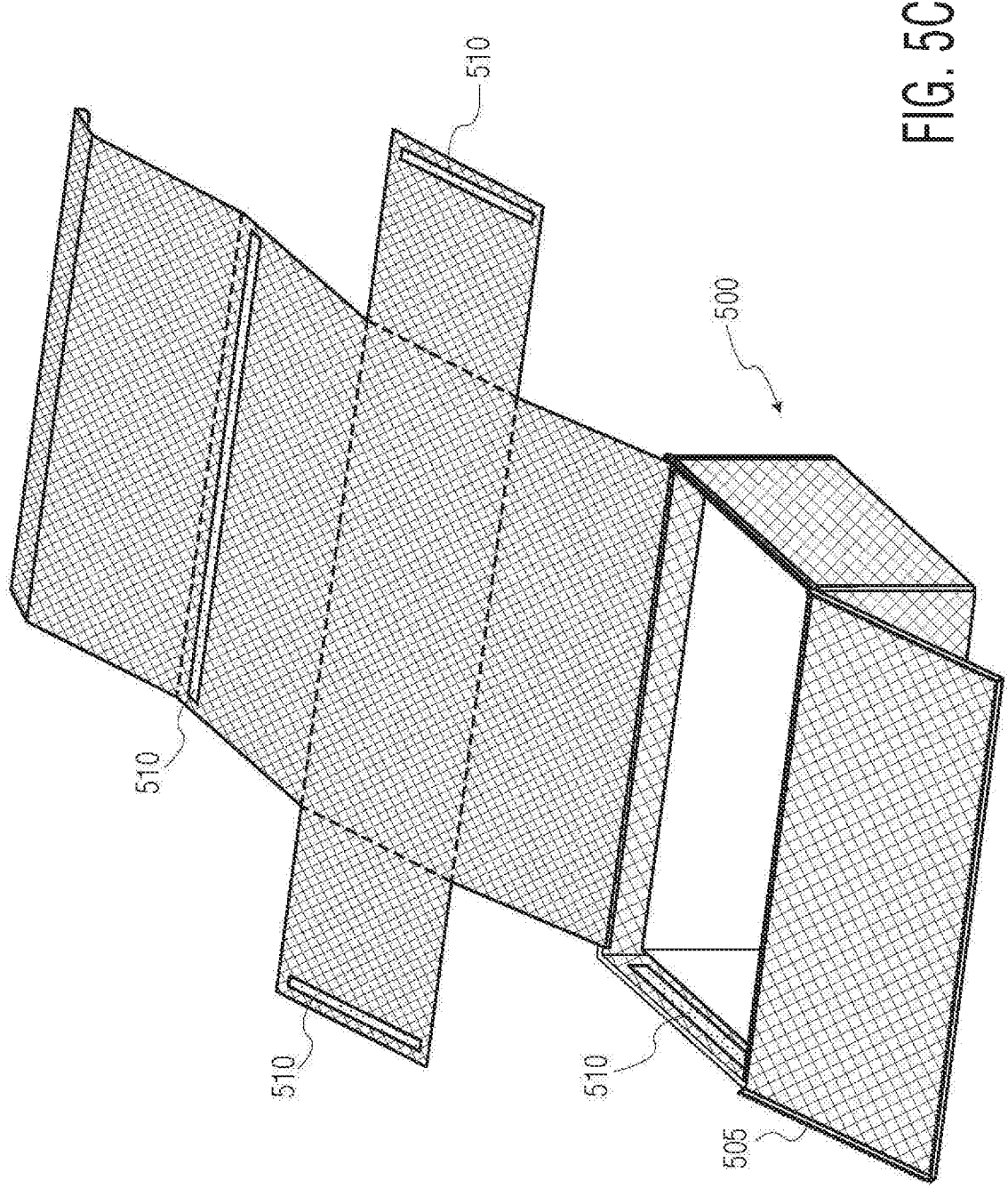

FIGS. 5A, 5B and 5C show the implementation of the invention in a cubed shaped container 500 which includes a top sealable rubberized zipper 505. FIG. 5B illustrates the cubed shaped container 500 with the top of the cube unzipped and opened. FIG. 5C illustrates the use of hook and fastener attachment system 510 to ensure the inside portions of the cube are properly positioned for use and contain an activated carbon filter (not shown). Also shown in FIG. 5C is the mesh lining 515 pulled out for visualization purposes.

Figure 6A:
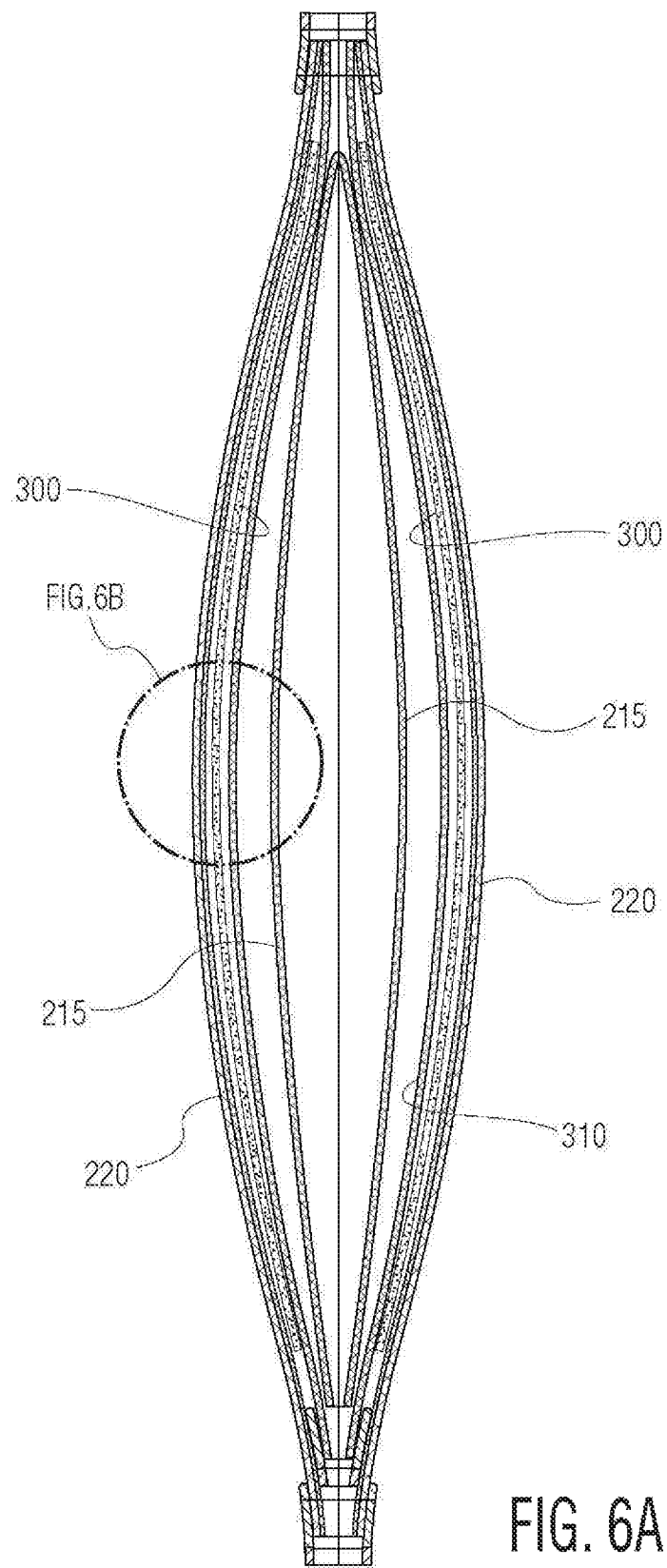
FIGS. 6A, 6B and 6C show cross sections of the sack or container of FIG. 2.
Figure 6B:
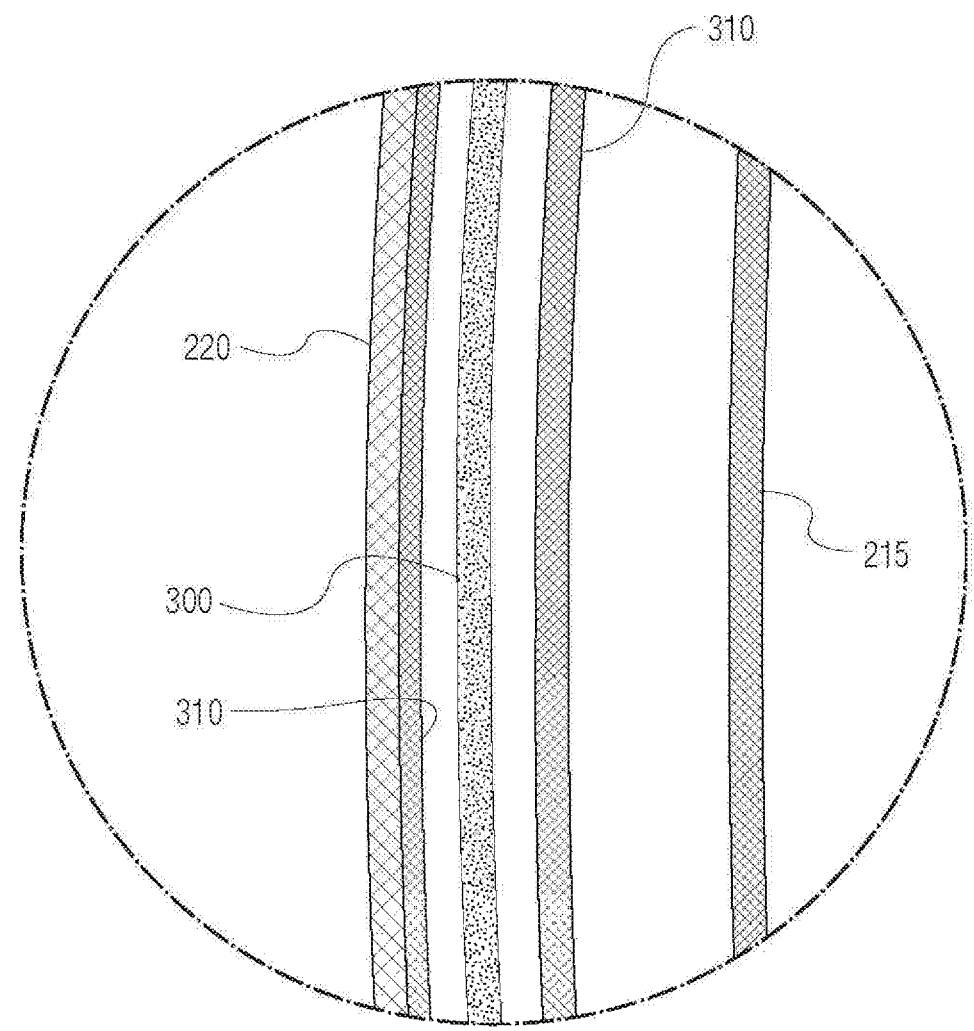
Figure 6C:
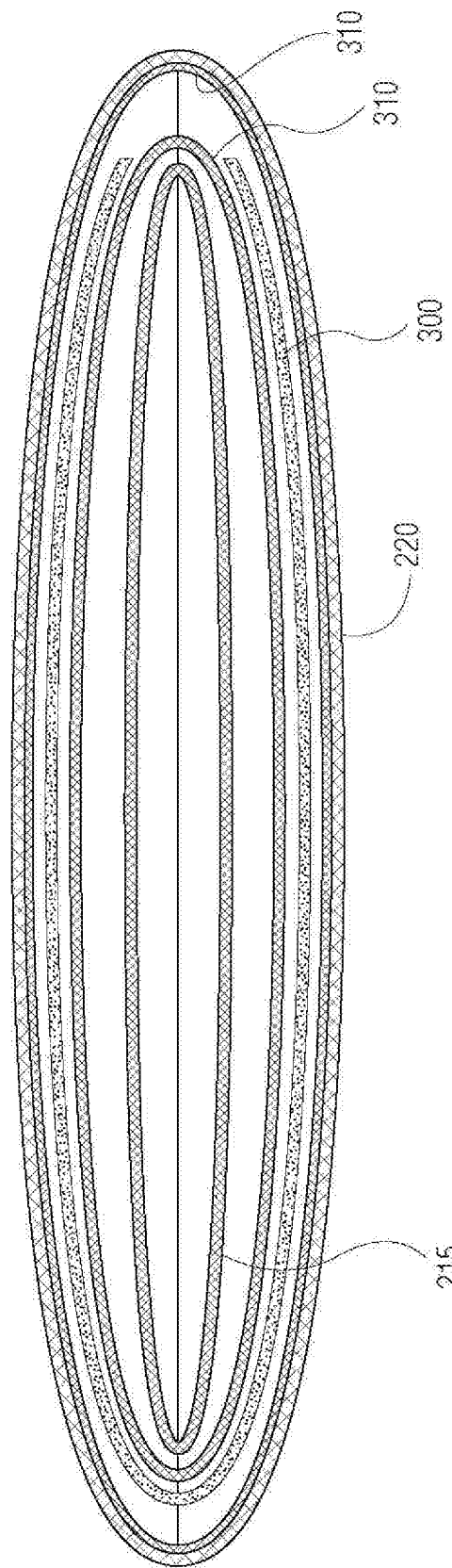

FIGS. 6A, 6B & 6C show cross sectional illustrations of the sack 200 along the reference lines identified in FIG. 2. As shown in FIGS. 6A-6C, working from the outside of the sack 200 to the inside, the sack 200 includes a second container 220, the outside wall of a mesh filter container 310, the activated carbon filter 300, the inside wall of a mesh filter container 310, and the first container 215.

One of ordinary skill in the art would appreciate that in another embodiment of the present invention, the mesh filter container may be replaced with a compartment on the inside wall of the second container 220 in either the non-extendable embodiment or the extendable embodiment. In this embodiment, the activated carbon filter would be positioned within zippered pocket (or similar compartment) which is built into the inside wall of the second container 220. In another embodiment of the non-extendable embodiment of the present invention, the mesh filter container may be replaced with a compartment on the outside wall of the first container 215.

Figure 7A:
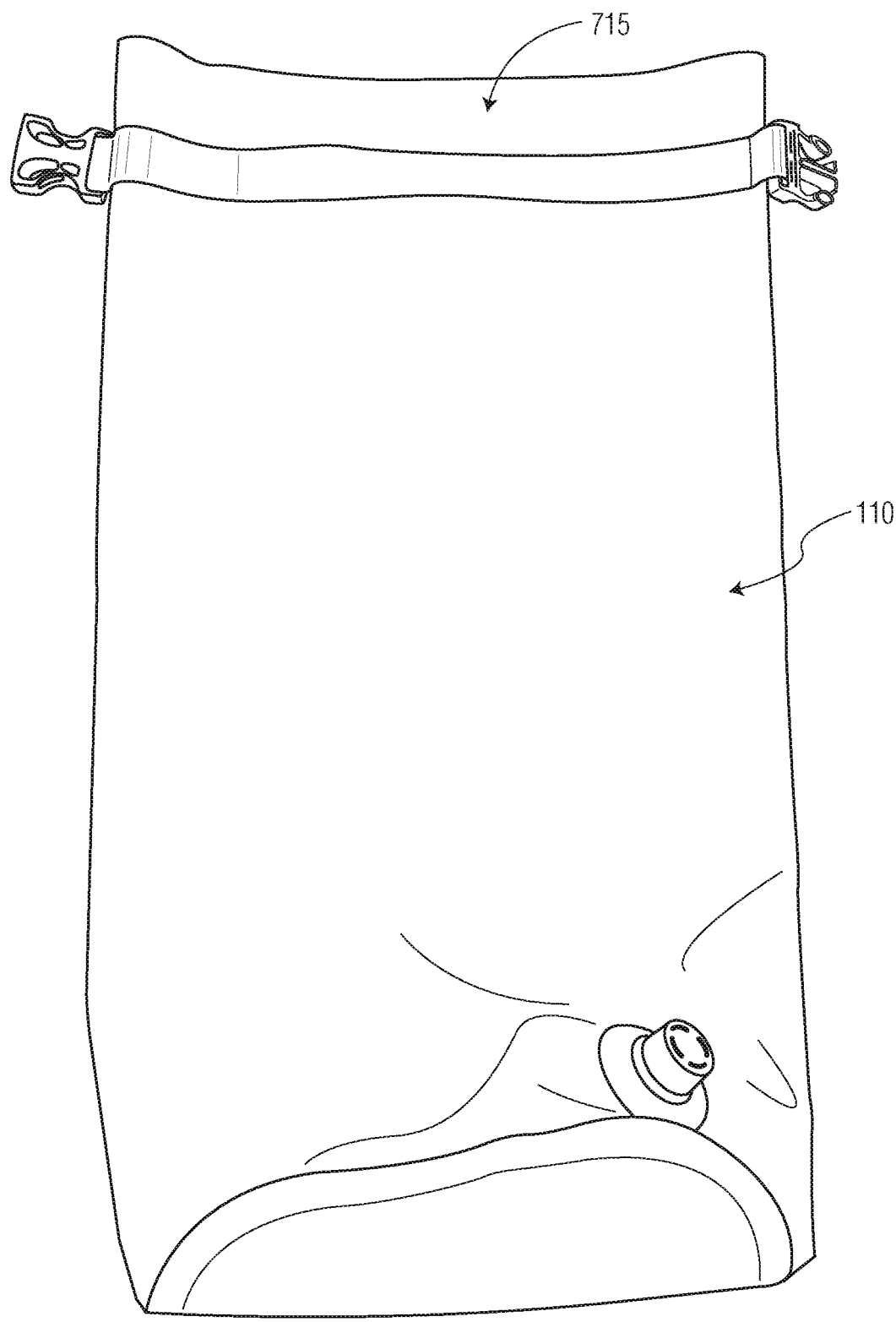
FIGS. 7A, 7B, and 7C illustrate another embodiment of the invention in a non-extendable single container embodiment.
Figure 7B:
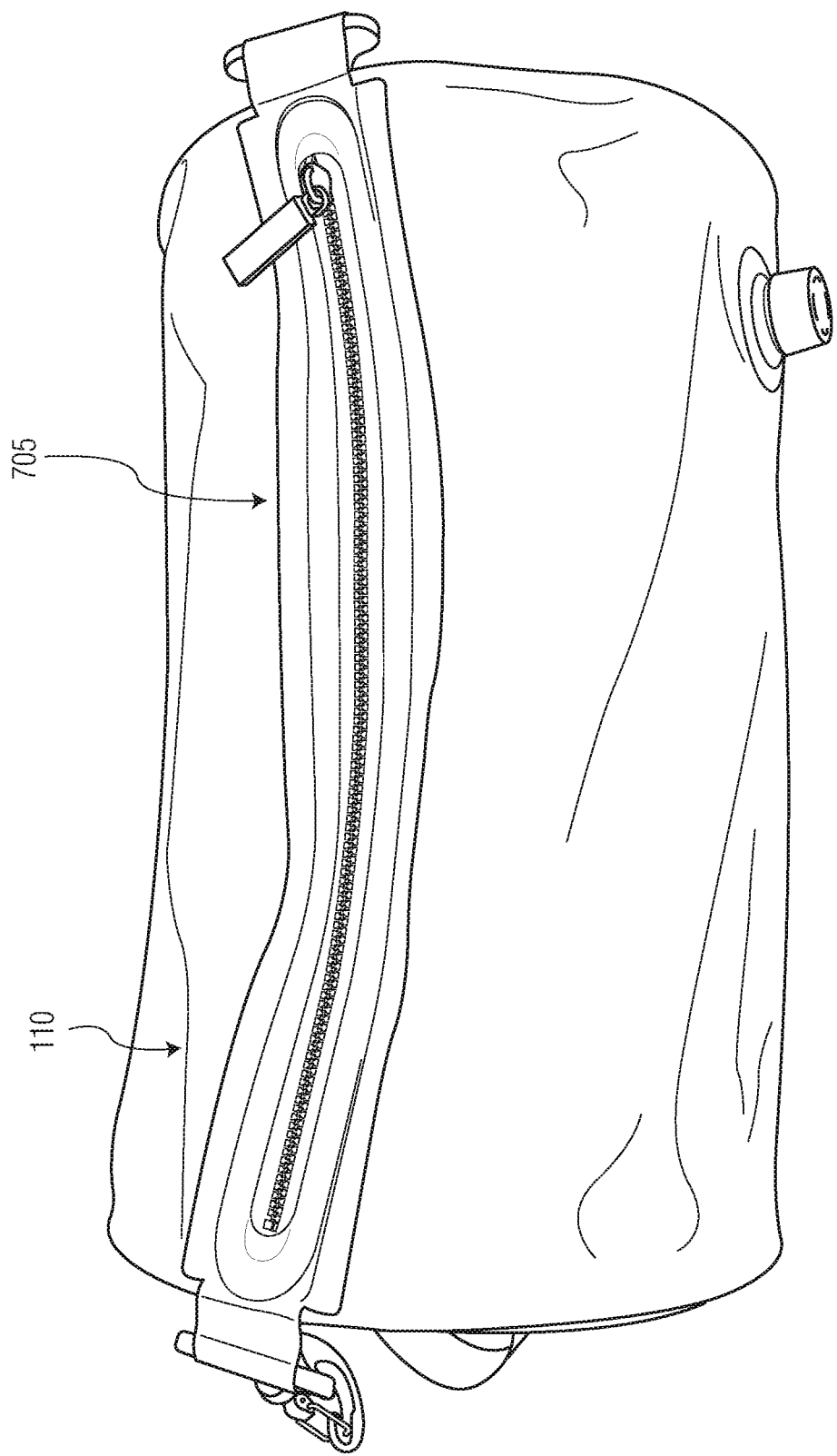
Figure 7C:
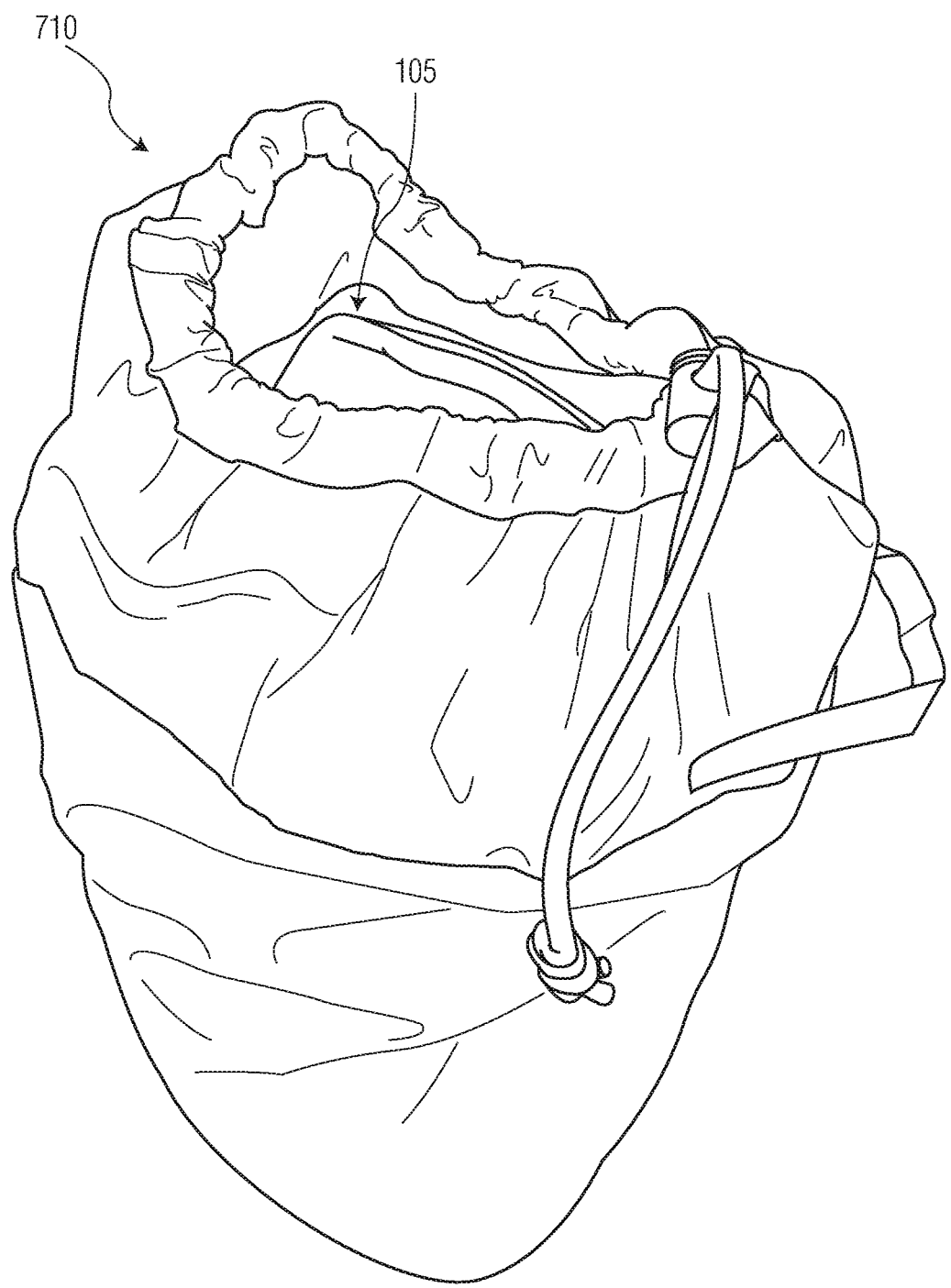

Referring now to FIGS. 7A-7I a non-extendable single container embodiment of the present invention includes a top opening 105 (FIG. 7C), and a container 110 (FIG. 7A). The container 110 is closed by either sliding a sealable rubberized zipper 705 side to side (FIG. 7B), pulling a drawstring 710 which encircles the top opening of the container (FIG. 7C) or a roll and buckle 715 enclosure where the top of the bag is rolled and held in place by connecting buckle ends one either end of the bag (FIG. 7A). In this non-extendable single embodiment, the container 110 may be made, for example, of 3 materials/fabrics, a waterproof fabric made of a soft fabric made ideally of nylon, polyester and lined with a Thermoplastic Polyurethane (TPU) membrane for waterproofing, or made entirely of TPU. In either configuration, antimicrobial is added to both the inside and outsides of the fabric/materials to combat the formation of bacterial and fungi.

Figure 7D:
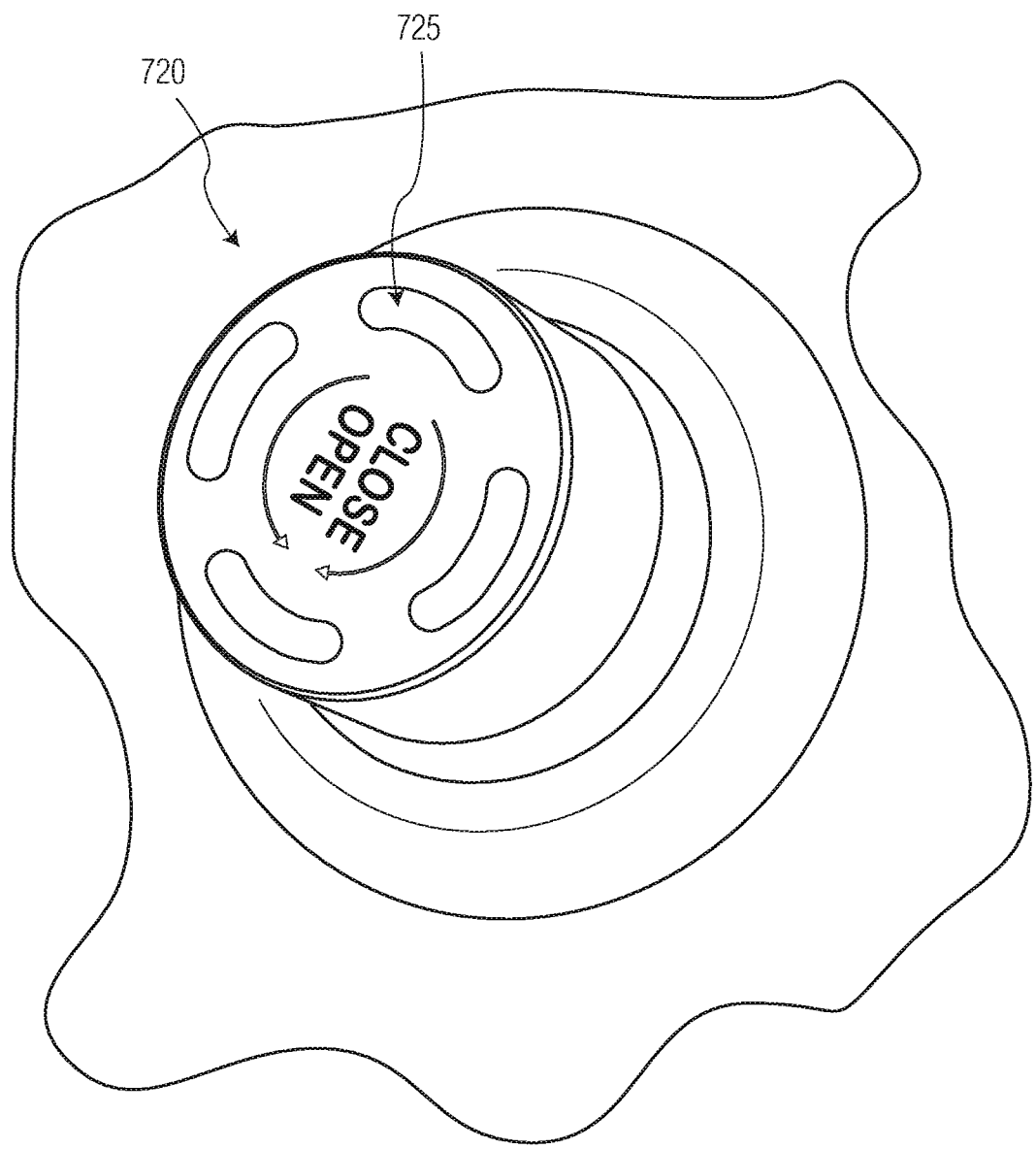
FIGS. 7D, 7E, 7F, 7G, 7H and 7I illustrate features of the embodiment shown in FIGS. 7A-7C.
Figure 7E:
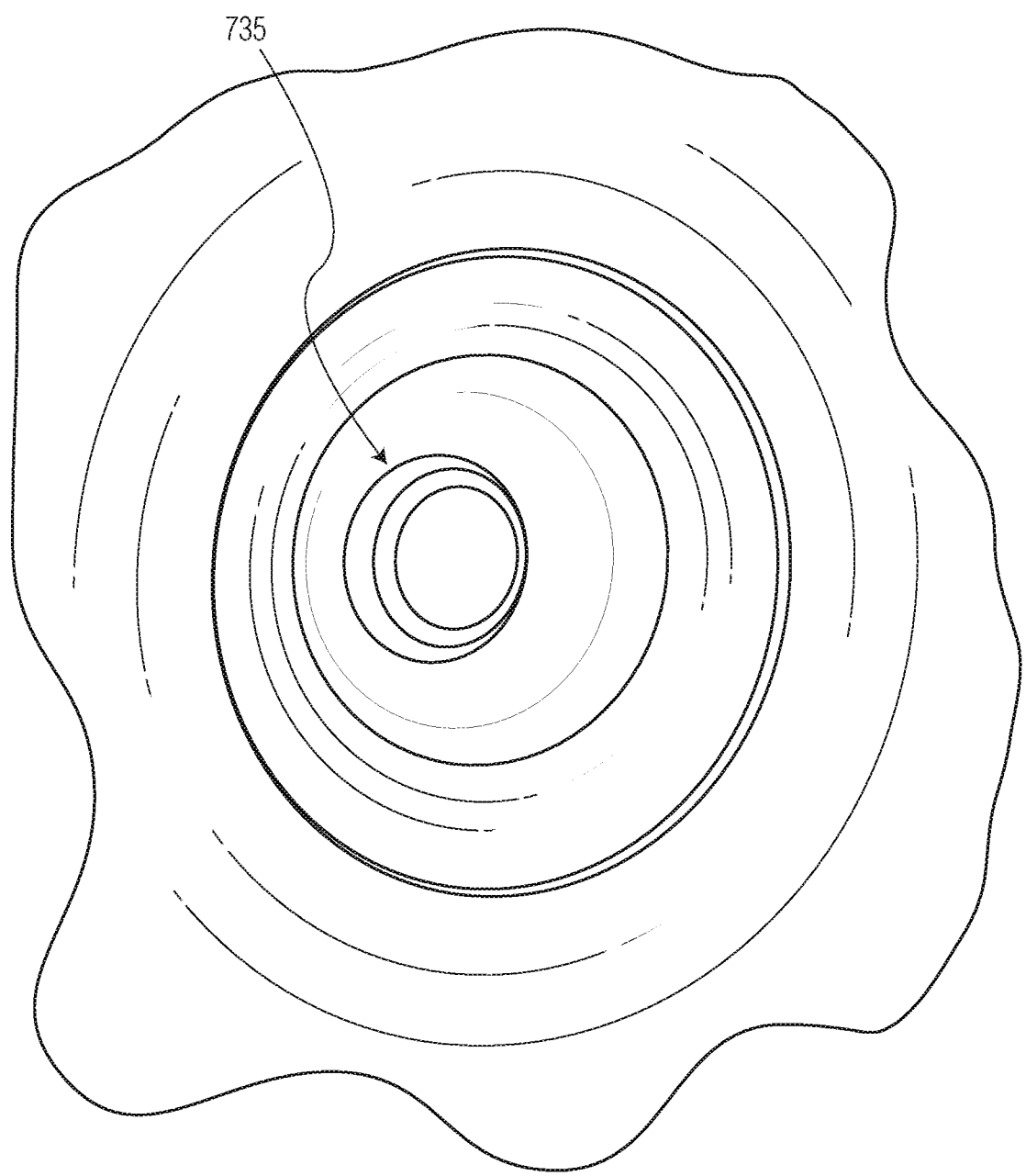
Figure 7F:
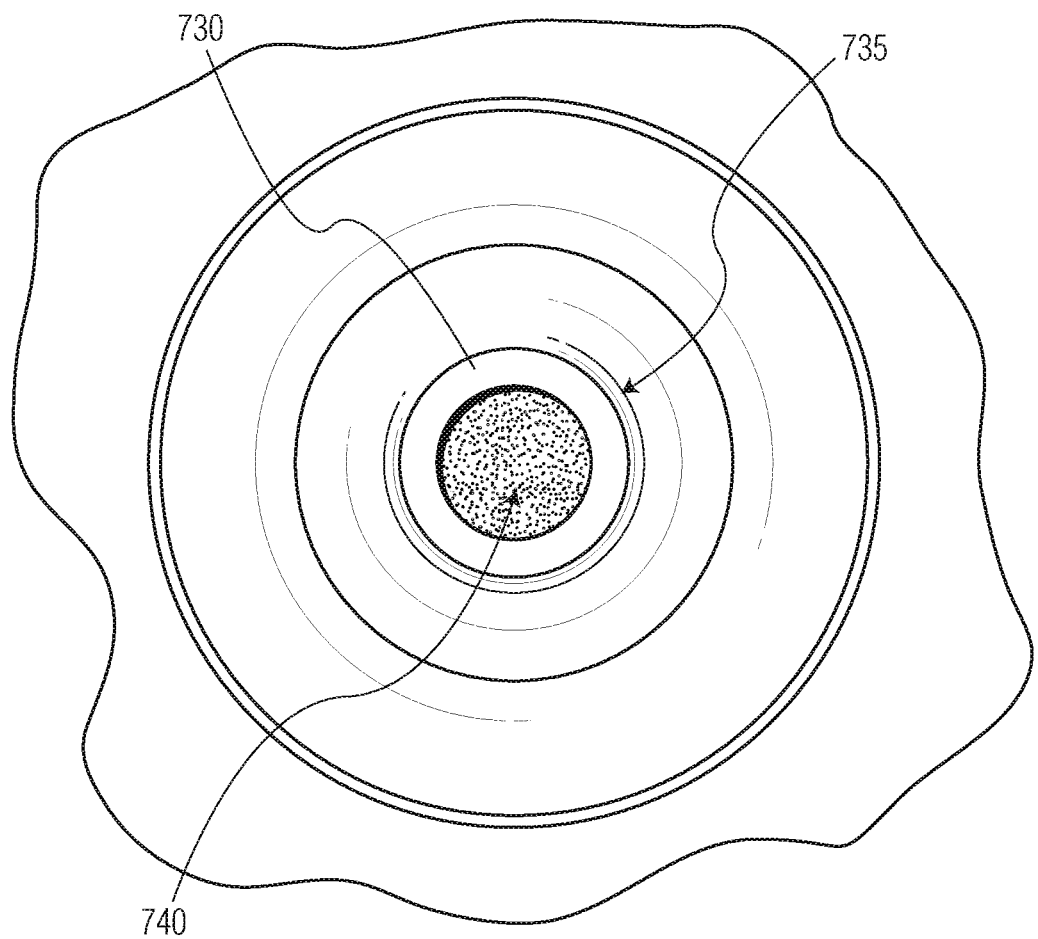
Figure 7G:
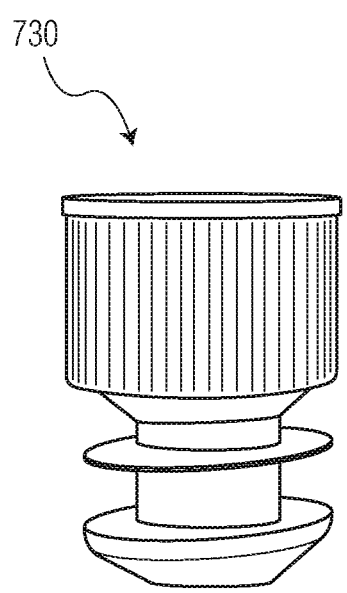
Figure 7H:
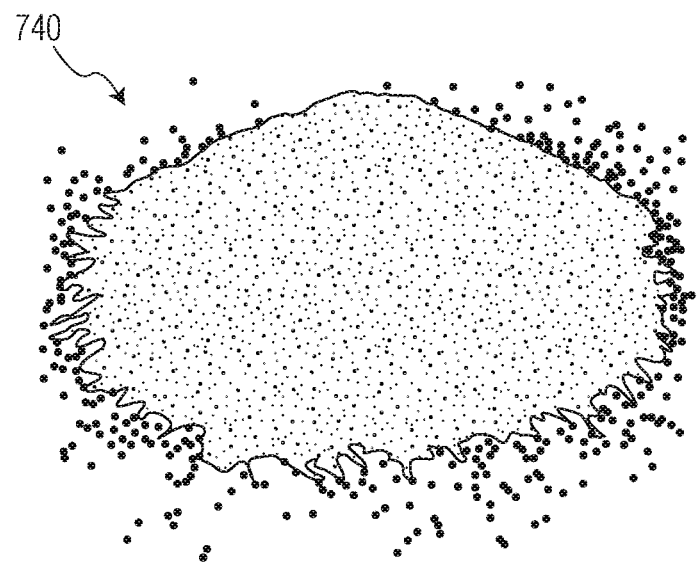
Figure 7I:
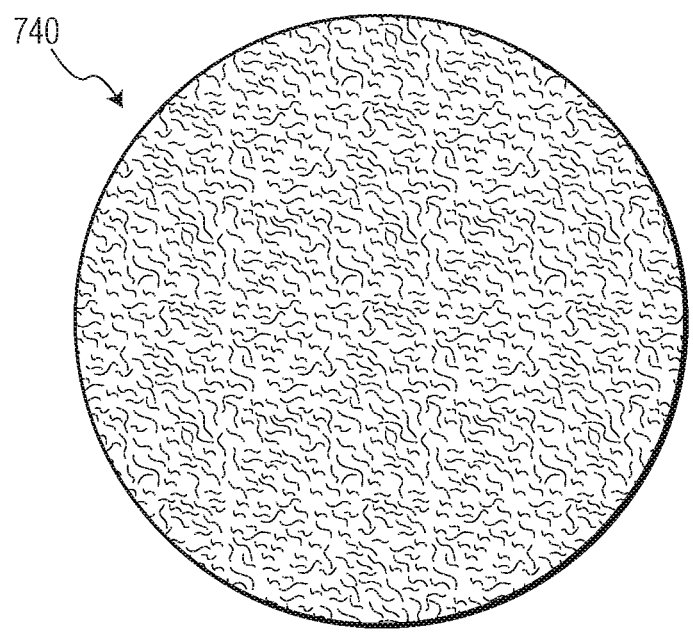

In FIGS. 7D, 7E and 7F, the non-extendable single container embodiment can also be fitted with an air valve 720 (FIG. 7D) which may be opened to permit air to exit the sack by turning the air valve knob 725 (FIG. 7D), for example, to the left. In the open position, the sack may be compressed to remove excess air to: 1) fit more tightly inside luggage or backpacks, 2) to deprive mold the oxygen needed to grow and 3) promotes greater contact between the bag's antimicrobial material and the contents of the sack. While compressed, the air valve 720 may be closed by turning the air valve knob 725, for example, to the right, preventing air from re-entering the sack. While in open position, air can freely exit the sack. Additionally, an activated carbon filter 730 (FIG. 7F and FIG. 7G) may be added to the entrance of the valve 735 (FIG. 7F) to absorb odor or moisture from permeating to and effecting clothing or possessions outside of the sack. The activated carbon filter 730 may be added by pressing the filter 730 securely inside the entrance of the valve 735 (FIG. 7F). Once added, the activated carbon filter 730 channels any air exiting the sack through the activated carbon material 740 (FIGS. 7F, 7H and 7I) contained within. As shown in FIG. 7F, the activated carbon material 740 contains porous carbon, which absorbs odor and moisture from the air exiting the container 110.

Unless defined otherwise, all technical terms used herein have the same meaning as commonly understood by one of ordinary skill in the art to which this invention belongs. Any methods and materials similar or equivalent to those described herein also can be used in the practice or testing of the present disclosure.

While the present disclosure has been described with reference to the specific embodiments thereof, it should be understood by those skilled in the art that various changes may be made and equivalents may be substituted without departing from the true spirit and scope of the invention. For example, while the invention has been described with respect to a rectangular sack, the invention can also be implemented in container of other shapes and sizes, such as a cube, a rectangle, or even a triangle. In addition, many modifications may be made to adopt a particular situation, material, composition of matter, process, process step or steps, to the objective spirit and scope of the present disclosure. All such modifications are intended to be within the scope of the claims appended hereto.

What is claimed is:

1. A non-expandable sack comprising:
   a first container accessible through a top opening;
   a second container accessible through said top opening;
   an activated carbon filter positioned within a space between said first container and said second container such that a first side of said activated carbon filter is facing one side of said first container and a second side of said activated carbon filter is facing one side of said second container;
   wherein said top opening can be accessed through a top sealable rubberized zipper;
   said activated carbon filter is positioned such that it may absorb at least a portion of odor and moisture from items stored inside said first container and
   at least a portion of the material which the sack is comprised of is infused with a antimicrobial additive.

2. The non-expandable sack of claim 1, wherein walls of the first container are made of a breathable polyester mesh material.

3. The non-expandable sack of claim 1, where walls of the second container are made of a breathable polyester mesh material.

4. The non-expandable sack of claim 1, wherein the walls of the first container and the walls of the second container are each made of a breathable polyester mesh material.

5. The non-expandable sack of claim 1, including a mesh filter container in which said activated carbon filter is positioned.

6. The non-expandable sack of claim 1, including a filter container zipper located on an inside wall of said second container in which said activated carbon filter is positioned.

7. The non-expandable sack of claim 1, including a filter container zipper located on an outside wall of said first container in which said activated carbon filter is positioned.

* * * * *